US009168299B2

(12) United States Patent
Hernell et al.

(10) Patent No.: US 9,168,299 B2
(45) Date of Patent: *Oct. 27, 2015

(54) METHODS FOR TREATING JUVENILE ARTHRITIS WITH ANT-BILE SALT-STIMULATED LIPASE (BSSL) ANTIBODIES

(71) Applicant: LipUm AB, Umea (SE)

(72) Inventors: Olle Hernell, Umea (SE); Susanne Lindquist, Roback (SE); Lennart Gustav Lundberg, Billdal (SE)

(73) Assignee: LIPUM AB, Umea (SE)

( * ) Notice: Subject to any disclaimer, the term of this patent is extended or adjusted under 35 U.S.C. 154(b) by 0 days.

This patent is subject to a terminal disclaimer.

(21) Appl. No.: 14/067,495

(22) Filed: Oct. 30, 2013

(65) Prior Publication Data
US 2014/0099323 A1    Apr. 10, 2014

Related U.S. Application Data

(63) Continuation of application No. 13/262,805, filed as application No. PCT/SE2010/050377 on Apr. 6, 2010, now Pat. No. 8,597,650.

(60) Provisional application No. 61/254,221, filed on Oct. 23, 2009.

(30) Foreign Application Priority Data

Apr. 8, 2009 (SE) ...................... 0950228

(51) Int. Cl.
A61K 39/395 (2006.01)
C07K 16/40 (2006.01)
C12N 9/20 (2006.01)
A61K 31/7105 (2006.01)
A61K 39/00 (2006.01)

(52) U.S. Cl.
CPC ......... *A61K 39/3955* (2013.01); *A61K 31/7105* (2013.01); *C07K 16/40* (2013.01); *C12N 9/20* (2013.01); *A61K 2039/505* (2013.01)

(58) Field of Classification Search
None
See application file for complete search history.

(56) References Cited

U.S. PATENT DOCUMENTS 8,597,650 B2 * 12/2013 Hernell et al. ............. 424/146.1
2007/0172485 A1   7/2007 Lombardo et al.

FOREIGN PATENT DOCUMENTS

| EP | 1840573 A1 | 10/2007 |
| WO | 2007-063405 A2 | 6/2007 |
| WO | 2008148884 A1 | 12/2008 |
| WO | 2009086096 A2 | 7/2009 |

OTHER PUBLICATIONS

International Search Report and Written Opinion issued on Jun. 4, 2010 for International Application No. PCT/SE2010/050377.
McKillop, et al., "Characterization of the C-terminal region of molecular forms of human milk bile salt-stimulated lipase", ACTA Paediatrica, Universitetsforlaget, Oslo, No, vol. 93, No. 1, 2004, pp. 10-16.
Supplementary Extended Search Report dated Nov. 26, 2012 for Application No. 10 76 1935 corresponding to International Application No. PCT/SE2010/050377.
Lindquist, et al., "Bile Salt-Stimulated Lipase Plays an Unexpected Role in Arthritis Development in Rodents", Plos One 7:1-8, Oct. 2012.
Williams, Autoimmune Disease: Animal Models. In: Encyclopedia of Life Sciences (LS). John Wiley & Sons, Ltd: Chichester. DOI: 1002/978047001 5902.s0001436.pub2 (Oct. 2010).
Sampath Prahalad and David N. Glass, "Is juvenile rheumatoid arthritis/juvenile idiopathic arthritis different from rheumatoid arthritis?", Arthritis Research 2002, vol. 4, Suppl 3, pp. 303-310.

* cited by examiner

*Primary Examiner* — Phillip Gambel
(74) *Attorney, Agent, or Firm* — Knobbe, Martens, Olson & Bear, LLP

(57) ABSTRACT

It provides methods and pharmaceutical compositions comprising antagonists to the protein Bile Salt-Stimulated Lipase (BSSL) for the prevention, prophylaxis and treatment of inflammatory diseases, such as rheumatoid arthritis. It further relates to pharmaceutical compositions comprising BSSL antagonists and their use in methods for the prevention, prophylaxis and treatment of inflammatory diseases, such as rheumatoid arthritis. Suitable BSSL antagonists to be used according to the invention are BSSL antibodies.

2 Claims, 24 Drawing Sheets

METHODS FOR TREATING JUVENILE ARTHRITIS WITH ANT-BILE SALT-STIMULATED LIPASE (BSSL) ANTIBODIES

RELATED APPLICATIONS

This application is a Continuation application of U.S. application Ser. No. 13/262,805, filed Jan. 9, 2012, now U.S. Pat. No. 8,597,650 which is a U.S. National Phase of International Application No. PCT/SE2010/050377, filed Apr. 6, 2010, designating the U.S., and published as WO 2010/117325 on Oct. 14, 2010, which claims the benefit of U.S. Provisional Application No. 61/254,221 filed Oct. 23, 2009, and Swedish Patent Application No. 0950228-7 filed Apr. 8, 2009.

SEQUENCE LISTING

This application incorporates by reference the sequence listing of record in application Ser. No. 13/262,805.

TECHNICAL FIELD OF THE INVENTION

The invention provides methods and pharmaceutical compositions comprising antagonists to the protein Bile Salt-Stimulated Lipase (BSSL) for the prevention, prophylaxis and treatment of inflammatory diseases, such as rheumatoid arthritis. The invention further relates to pharmaceutical compositions comprising BSSL antagonists and their use in methods for the prevention, prophylaxis and treatment of inflammatory diseases, such as rheumatoid arthritis.

BACKGROUND OF THE INVENTION

Inflammatory Diseases—Rheumatoid Arthritis

Inflammation, a reaction of the body to injury or to infectious, allergic, or chemical irritation can lead to a variety of inflammatory diseases or disorders such as inflammation associated with allergy, inflammation related to the production of nitric oxide, inflammation related to the skin, abdomen, peripheral or central nervous system, eye or tear glands, ear, nose, mouth, lung, heart, liver, pancreas, thyroid, adipose tissue, kidney, joints or blood vessels, or inflammation related to infection, trauma or autoimmunity.

Rheumatoid arthritis (RA) is a chronic, inflammatory, systemic autoimmune disease that affects about 1% of the general population in Western societies (Gabriel 2001). The disease process results in progressive destruction of joint cartilage and bone. This destruction results from immune responses and non-antigen-specific innate inflammatory processes. The disease is characterized by mono- or polyarticular joint inflammation with massive accumulation of neutrophils in the synovial fluid and tissue. The synovial neutrophils contribute to cartilage destruction by releasing proteases and generating oxidants and it is becoming more and more evident that inhibiting neutrophil infiltration into inflamed joints could be an approach to prevent progression of the disease (Hallett 2008). Current therapies for RA include non-steroid anti-inflammatory drugs (NSAIDs) for pain treatment, disease-modifying antirheumatic drugs (DMARDs) and biological agents that target specific proinflammatory cytokines, or cell surface receptors of various cell types.

There remains a need, however, for alternative pharmaceutical treatments of inflammatory diseases, especially chronic inflammatory diseases. Consequently there is a need to identify new unique targets involved in inflammatory signalling and processes, which can be used as the basis for development of new innovative therapeutic agents for the treatment, prophylaxis and prevention of inflammatory diseases.

Bile Salt-Stimulated Lipase

The bile salt-stimulated lipase (BSSL) also designated carboxyl ester lipase (CEL) or bile salt-dependent lipase (BSDL) is a lipolytic enzyme expressed in the exocrine pancreas and secreted into the intestinal lumen in all species so far investigated. In some species, including the human, BSSL is also expressed by the lactating mammary gland and secreted with the milk. BSSL has broad substrate specificity with capacity to hydrolyze a variety of different substrates, e.g. cholesteryl esters, tri-, di-, and monoacylglycerols, fat-soluble vitamin esters, phospholipids, galactolipids and ceramides (Hui and Howles 2002). The physiological function of BSSL was originally thought to be confined to the small intestine and hydrolysis of dietary fat (Hernell et al. 1997). The high abundance of BSSL in pancreatic juice (up to 5% of total protein content) and the ability of BSSL to hydrolyze a broad spectrum of lipids have led researchers to suggest a variety of functions for BSSL in lipid digestion and absorption. BSSL has a key role in the absorption of cholesteryl esters (Fait et al. 2002), verified in mice lacking the BSSL (CEL gene) (Howles et al. 1996). While this is considered its main function in the human adult it is likely to contribute also to triglyceride digestion and absorption in the newborn infant (Lindquist and Hernell 2010).

BSSL was found to be present in low, but significant levels in serum of healthy individuals (Bläckberg et al. 1985) and current research has implicated that BSSL is involved in lipoprotein metabolism and modulation of atherosclerosis (Hui and Howles 2002). The potential function, or even the question if elevated levels of circulating BSSL is a risk factor for, or protects against atherosclerosis is not clear. A surprisingly strong positive association between BSSL, assayed as cholesterol esterase activity, and total—as well as low-density lipoprotein (LDL)-cholesterol levels in serum was first reported (Hui and Howles 2002). BSSL was then shown to be associated with smooth muscle cells (SMCs) within atherosclerotic plaques and to induce vascular SMC proliferation in vitro (Auge et al. 2003). A study, using transgenic mice, demonstrated that macrophage expression of BSSL is pro-atherogenic, favouring cholesteryl ester accumulation and foam cell formation (Kodvawala et al. 2005). Judged by these studies BSSL would be a risk factor for atherosclerosis. On the other hand, BSSL reduces lysophosphatidylcholine content in oxidized LDL, thereby reducing accumulation of oxidized LDL in macrophages (Hui and Howles 2002), and it has been suggested to play a physiological role in hepatic selective uptake and metabolism of high density lipoprotein cholesteryl esters by direct and indirect interactions with the scavenger receptor BI pathway (Camarota et al. 2004), which implicates that BSSL in serum protects against atherosclerosis.

The BSSL Protein

The human BSSL protein (encoded by the CEL gene) is a single-chain glycoprotein of 722 amino acids (Nilsson et al. 1990). The enzyme is synthesised as a precursor of 742 amino acids with a signal peptide of 20 amino acids. Two bile salt-binding sites regulating the activity of the enzyme and the resistance to proteases have been postulated (Hui 1996) as well as a sphingolipid binding domain (SBD) (Aubert-Jousset et al. 2004).

Schematically the enzyme can be divided into two parts:

i) The N-terminal domain with a striking homology to acetylcholinesterase and some other esterases. In this part the proposed catalytic triad (Ser194 (included in the motif GESAG), Asp320 and His435) are found as well as a N-glycosylation site, Asn187, a heparin-binding site (postulated to be located at position 1-100) and the two intra chain disulfide bridges (Cys64-Cys80 and Cys 246-Cys257). The heparin binding ability has been found to be located in the part of the molecule consisting of amino acids 1-445 (Spilburg et al. 1995) and the heparin binding domain may, in fact, be a three-dimensional structure composed of different sequences. The heparin binding properties of BSSL is thought to be important for interactions with cell membranes, exemplified by intestinal cell membranes (Fält 2002).

ii) The C-terminal part (encoded by exon 11) with a variable number of tandem repeats (VNTR)-region containing similar but not identical repeats (11 amino acids). The most common human form contains 16, but there is a variation in number of repeats both between individuals and alleles (Lindquist et al. 2002). The repeats are followed by an extra tail of 11 amino acids (this tail is longer in the corresponding rat and mouse enzyme). The repeats are proline-rich and the presence of aspartic acid in every repeating unit and glutamic acid in some, render this region highly acidic and contributes to the low iso-electric point of the protein. The number of proline-rich repeats has been reported to vary extensively between species, typically ranging from three in mouse and the cow, four in the rat to 16 in humans and 39 in the gorilla (Hui and Howles 2002; Madeyski et al. 1999). This diversity in number of repeated units can explain the observed size differences of the protein between species; the mouse BSSL is a 74 kDa protein while the human BSSL, which is extensively glycosylated across the repeated region, has an apparent molecular mass of 120-140 kDa; the repeats carry most of the 15-35% carbohydrate of the protein. The varying apparent molecular mass can be explained both by the number of repeats and differences in glycosylation (Lindquist et al. 2002). It has been shown by analysing the isolated C-terminal part of human milk BSSL (amino acids 528-722) that probably only 10 out of 16 repeats in human milk BSSL are O-glycosylated (Wang et al. 1995).

It has been suggested that the repeats may have a functional role in protecting BSSL from proteolytic degradation and that their O-glycosylation is important for secretion of the enzyme (Bruneau et al. 1997). The oligosaccharides in the C-terminal region contain Lewis x and Lewis b and less Lewis a antigenic structures. Owing to those blood-group-related antigenic determinants, the C-terminal region of BSSL may have an adhesive function in cell-cell interactions, as illustrated by its antimicrobial effects (Naarding et al. 2006; Ruvoën-Clouet et al. 2006). On the other hand, the repeated region may be less important for catalytic activity, activation by bile salts and heparin binding (Hui 1996).

The C-tail has also been suggested to be an important structural part by binding to a lectin-like receptor (LOX-1) on the surface of intestinal endothelium cells (Fayard et al. 2003). The heparin binding site(s) forms the other binding part, and these binding sites have a pivotal role in the mechanism of action for BSSL in different cellular environments and cell stages.

Vascular BSSL

Comparison of BSSL VNTR genotype and serum lipid phenotype revealed an association between the number of repeats and serum cholesterol profile (Bengtsson-Ellmark et al. 2004). While it is possible that the repeat polymorphism is merely a genetic marker for lipid profile, it is also possible that it has functional role in determining plasma lipid composition.

A wider role for BSSL in lipid metabolism is implicated by the presence of BSSL in human plasma and aortic tissue. The source of circulating BSSL has been discussed extensively. Human macrophages and endothelial cells were shown to synthesize and secrete the enzyme (Hui and Howles 2002). Conversely, in another study BSSL within atherosclerotic lesions was associated with smooth muscle cells (SMCs) but not with activated macrophages or endothelial cells (Auge et al. 2003). In yet another study, BSSL injected into rat intestinal loops was advocated to be internalized by enterocytes, transferred through the cells and released into the circulation (Bruneau et al. 2003). Based on these data it was proposed that circulating BSSL originates from the pancreas. However, it has been further shown that neither does the BSSL serum level increase after a meal of breast milk, nor does it differ between breastfed and formula fed human infants, although in the newborn breast milk is the major source of BSSL, while it is absent from infant formula (Bläckberg et al. 1985; Shamir et al. 2003).

An association of BSSL with apolipoprotein B-containing lipoproteins in human plasma has been reported (Bruneau et al. 2003), which together with the observation that BSSL is present in the human aorta and has the ability to modify low density lipoprotein (LDL) and high density lipoprotein (HDL) composition and reduce the atherogenicity of oxidized LDL (oxLDL) by decreasing their lysophosphatidylcholine (lysoPC) content (Shamir et al. 1996), invoked a potential new role for BSSL as a protective factor in the development of atherosclerosis. LysoPC is a major phospholipid component in oxLDL and is generated by oxidation and fragmentation of polyunsaturated fatty acids esterified to the sn-2 position of the PC molecule, followed by hydrolysis of the shortened fatty acyl residue by LDL-associated phosolipase A2 (PLA2) and BSSL. Although lysoPC constitutes only 1-5% of total PC in non-oxLDL, oxidative modification of LDL can raise this proportion to as high as 40-50%. LysoPC acts as a chemoattractant for monocytes, induces monocyte adhesion to the vascular endothelium and promotes macrophage proliferation, which eventually leads to foam cell formation. Due to its effects on lysoPC, it has been suggested that BSSL may interact with cholesterol and oxidized lipoproteins to modulate the progression of atherosclerosis (Hui and Howles 2002).

However, the fact that BSSL is found and accumulated in atherosclerotic lesions, and the fact that monocytes as well as macrophages (or SMC having a macrophage phenotype) express and secrete BSSL, indicate that these cells may be a possible source of the accumulated BSSL. The mechanism behind a pathophysiological role of BSSL in macrophages is suggested to be the function of BSSL as a ceramidase (Hui and Howles 2002) by its reduction of ceramide and lysophosphatidylcholine levels leading to increased cholesteryl ester accumulation in response to atherogenic lipoproteins resulting in increased atherosclerosis lesion size in vivo. This is in line with the study by Kodvawala et al. (2005), who by using in vivo models showed that BSSL expression in macrophages promotes cholesteryl ester synthesis and accumulation in response to modified LDL and increases atherosclerosis lesions in apoE deficient mice.

The Response to Retention Hypothesis of Atherosclerosis

Many of the processes implicated in the early stages of atherogenesis including endothelial damage, lipoprotein oxidation and macrophage and VSMC (vascular smooth muscle cells) proliferation are individually not sufficient to lead to lesion development. The response-to-retention hypothesis suggests that subendothelial retention of atherogenic lipoproteins is the trigger for all of these processes which are in fact normal physiological responses to the accumulation of lipids.

While the major determinant of initial retention of LDL is likely to be the proteoglycan composition within the subendothelial space, BSSL may facilitate and enforce retention once the lesion has started to form by acting as a molecular bridge between the subendothelial proteoglycans and lipoproteins (WO 2005/095986). The BSSL that is bound to the components of the extracellular matrix can act as bridging molecules in the retention of LDL, as suggested for Lipoprotein lipase (LPL) (Pentikainen et al. 2002).

BSSL in Platelets

Recently BSSL was found to be stored in blood platelets and released upon platelet activation (Panicot-Dubois et al. 2007). Moreover, BSSL was shown to induce calcium mobilization in platelets and to enhance thrombin-mediated platelet aggregation and spreading.

In a mouse thrombosis model (laser-induced injury), BSSL accumulated in arterial thrombi in vivo—at sites of vessel wall injury. When CXC chemokine receptor 4 (CXCR4) was antagonized, the accumulation of BSSL was inhibited and thrombus size was reduced. In BSSL knockout mice (BSSL-KO) tail bleeding times were increased in comparison with those of wild-type mice. These data suggest that BSSL modulates thrombus formation by interacting with CXCR4 on platelets.

CXCR4 belongs to the G-protein-coupled receptor (GPCR) gene family, and upon activation CXCR4 induces downstream signalling by several different pathways; e.g. CXCR4 binding of the chemokine ligand SDF-1 activates G-protein mediated signalling and induces cellular chemotactic responses (Clemetson et al. 2000). CXCR4 is also known to interact with HIV-1 and to act as a co-receptor for entry of the virus into cells. The binding of HIV-1 to CXCR4 is mediated via a domain denoted the V3 loop present on HIV-1 gp120. The BSSL protein contains a region that is structurally related to the V3-loop of gp120. This region, called the V3-like loop domain (amino acids 361-393) (Aubert-Jousset et al. 2004) was proposed to mediate the binding of BSSL to CXCR4 on platelets.

In summary, there are both confusing and conflicting result regarding the source and function of BSSL in plasma and aortic tissue.

EP 1840573 reports on differences in gene expression pattern between NOD (non-obese diabetic) mice positive or negative for insulin autoantibodies. 125 differentially expressed genes were identified, one of them being the CEL gene encoding BSSL. The differentially expressed genes are identified as having utility in early diagnosis of a pre-inflammatory state of autoimmune diseases, such as type I diabetes.

The differentially expressed genes are further suggested to be targets for the treatment of autoimmune diseases having a pre-inflammatory phase. It is well known in the art that expression of numerous genes is altered as a consequence of the development of a specific disease, as demonstrated in EP 1840573. However, all such differentially expressed genes can not be considered to be the cause of the development of the disease. On the contrary the identification of the causative gene(s), if at all existing, requires further complicated investigations. EP 1840573, even if identifying BSSL as potential marker for inflammatory disease, fails to identify BSSL as a cause for the development of inflammatory disease.

SUMMARY OF THE INVENTION

The present invention is based on the surprising discovery that BSSL has a role in inflammatory processes and that inhibition or elimination of BSSL protects from development of chronic arthritis in animal models.

The present invention is based on the demonstration that BSSL deficient mice are protected from development of inflammatory disease, exemplified by collagen-induced arthritis (CIA). Consequently antagonists to human BSSL are potentially useful for prevention, prophylaxis and/or treatment of inflammatory diseases. Suitable antagonists to BSSL are agents that reduce the activity, amount and/or expression of BSSL. Preferred BSSL antagonists which can be used according to the present invention are antibodies and antibody fragments specifically binding to human BSSL, as well as RNAi and antisense polynucleotides comprising sequences complementary to a polynucleotide sequences encoding human BSSL. Most preferably the BSSL antagonists to be used according to the invention are monoclonal BSSL antibodies.

Accordingly, one aspect of the present invention provides a method for the prevention, prophylaxis and/or treatment of an inflammatory disease comprising administering a pharmaceutical effective amount of an antibody or an antibody fragment specifically binding to human BSSL to a subject in need of such treatment.

Another aspect of the present invention provides a pharmaceutical composition comprising an antibody or an antibody fragment specifically binding to human BSSL, and a pharmaceutically acceptable carrier or excipient for use in the prevention, prophylaxis and/or treatment of an inflammatory disease.

Yet another aspect of the present invention provides use of an antibody or an antibody fragment specifically binding to human BSSL in the manufacture of a pharmaceutical composition for the prevention, prophylaxis and/or treatment of an inflammatory disease.

Another aspect of the present invention provides a method for the prevention, prophylaxis and/or treatment of an inflammatory disease comprising administering a pharmaceutical effective amount of an RNAi molecule or an antisense polynucleotide comprising a sequence complementary to a part of a polynucleotide sequence encoding human BSSL or a sequence complementary thereto to a subject in need of such treatment.

Another aspect of the present invention provides a pharmaceutical composition comprising an RNAi molecule or an antisense polynucleotide comprising a sequence complementary to a part of a polynucleotide sequence encoding human BSSL or a sequence complementary thereto, and a pharmaceutically acceptable carrier or excipient for use in the prevention, prophylaxis and/or treatment of an inflammatory disease.

Yet another aspect of the present invention provides use of an RNAi molecule or an antisense polynucleotide comprising a sequence complementary to a part of a polynucleotide sequence encoding human BSSL or a sequence complementary thereto in the manufacture of a pharmaceutical composition for the prevention, prophylaxis and/or treatment of an inflammatory disease.

Figure 1:
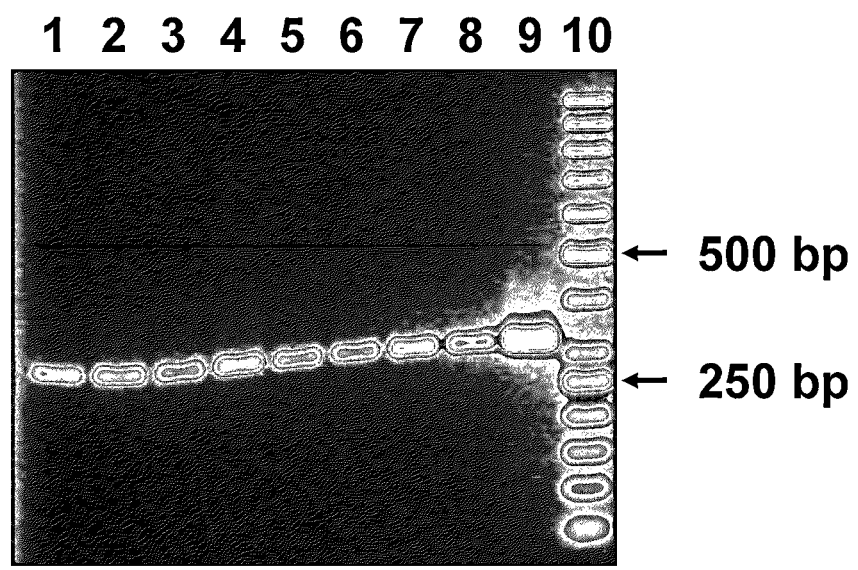
FIG. 1. Detection of BSSL mRNA in human liver.

Total RNA, isolated in duplicate from liver biopsies of four individuals, was reverse-transcribed and amplified using BSSL-specific oligonucleotide primers. The PCR products were resolved by 1.8% agarose gel electrophoresis and stained with ethidium bromide. A PCR product of the expected size (327 nt) was amplified from all samples; patient 1 (lanes 1 and 2); patient 2 (lanes 3 and 4); patient 3 (lane 5 and 6); patient 4 (lanes 7 and 8). cDNA synthesized from RNA isolated from human milk was used as a positive control (lane 9). The O'GeneRuler™ 50-bp DNA ladder (Fermentas, Ontario, Canada) was used as a molecular size marker (lane 10).

Figure 2:
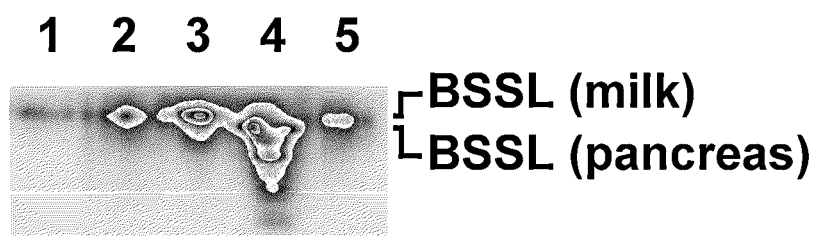

FIG. 2. Western blot.

Affinity-purified protein extracts derived from two human liver samples (patient no. 3 and no. 4), were separated by SDS-PAGE (10%), transferred to PVDF membranes, and probed with a polyclonal anti-human BSSL antibody. Patient 3, lane 1; patient 4, lane 2. Protein extracts from human milk, lane 3; human pancreas, lane 4; and BSSL purified from human milk, lane 5, were used as positive controls.

Figure 3:
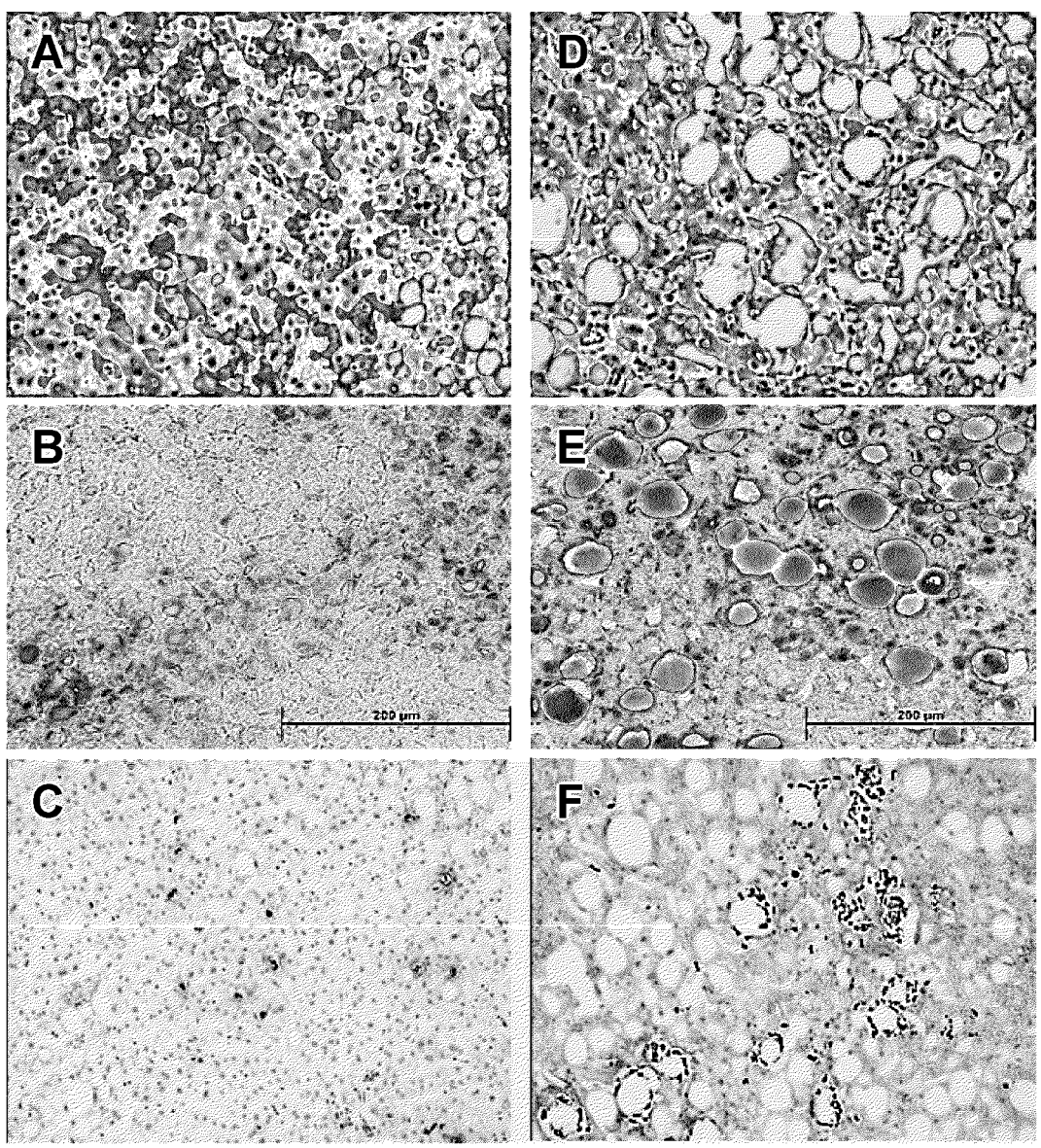

FIG. 3. Histology, oil red O staining, and BSSL localization in human liver sections.

Liver tissue sections (8-μm cryosections) obtained from two patients [patient 1 (A-C); patient 4 (D-F)] were stained with hematoxylin and eosin (A, D), oil red O (B, E), and immunohistochemistry with polyclonal anti-BSSL antibodies (C, F).

FIG. 4. Double immunofluorescence stainings against BSSL and immune cell markers.

BSSL co-localizes with CD15 but not with CD68-expressing cells in human liver. Double-immunofluorescence staining of liver sections (8 μm) obtained from two patients [patient 1 (panel 4A) and patient 4 (panel 4B)] using a rabbit polyclonal anti-BSSL antibody and mouse monoclonal anti-CD68 or anti-CD15 antibodies. A yellow color appeared in the merged picture in both panels when anti-BSSL and anti-CD15 antibodies were used together, seen as bright staining in these black and white figures, indicating co-localization.

Figure 5:
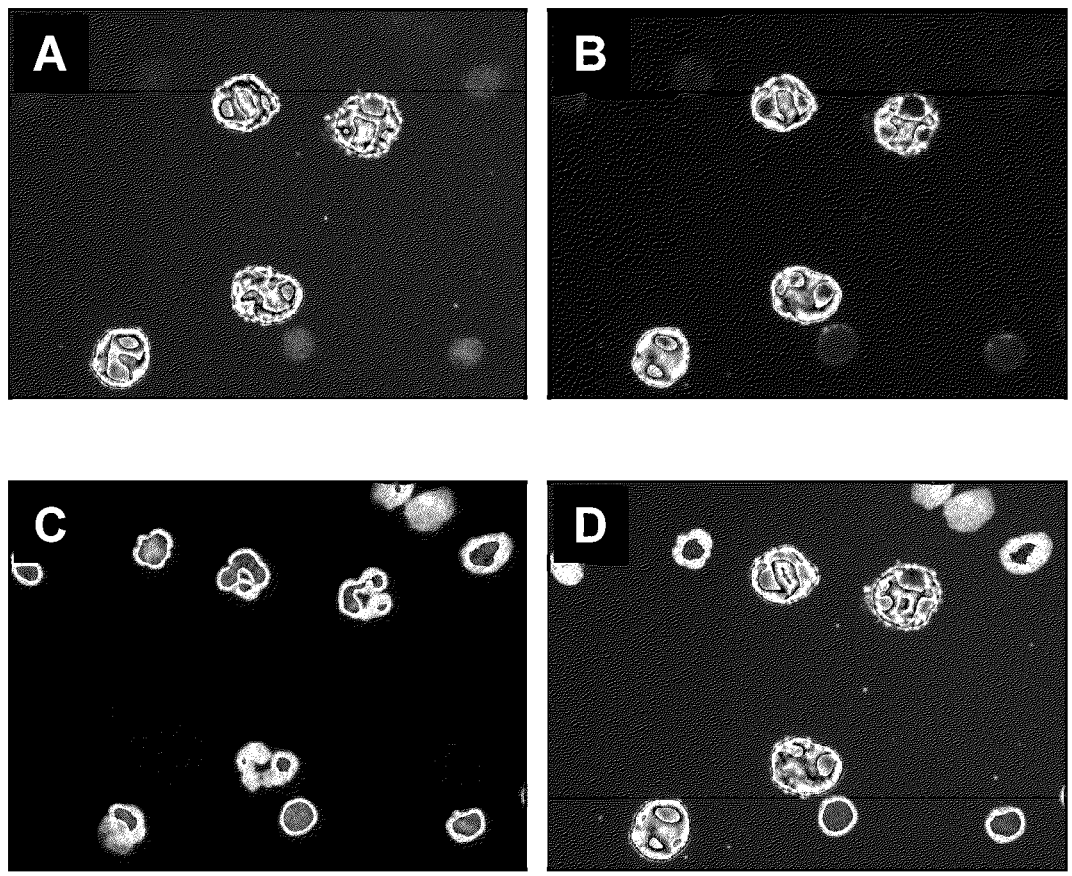

FIG. 5. BSSL localizes to circulating CD15-positive granulocytes.

Human leukocytes were harvested from blood of healthy volunteers, permeabilized and stained by double immunofluorescence using rabbit polyclonal anti-BSSL (A) and mouse monoclonal anti-CD15 (B) antibodies. Cell nuclei were counterstained with DAPI (C). A yellow color appeared in the merged picture (D), seen as bright staining in this black and white figure, indicating co-localization.

Figure 6:
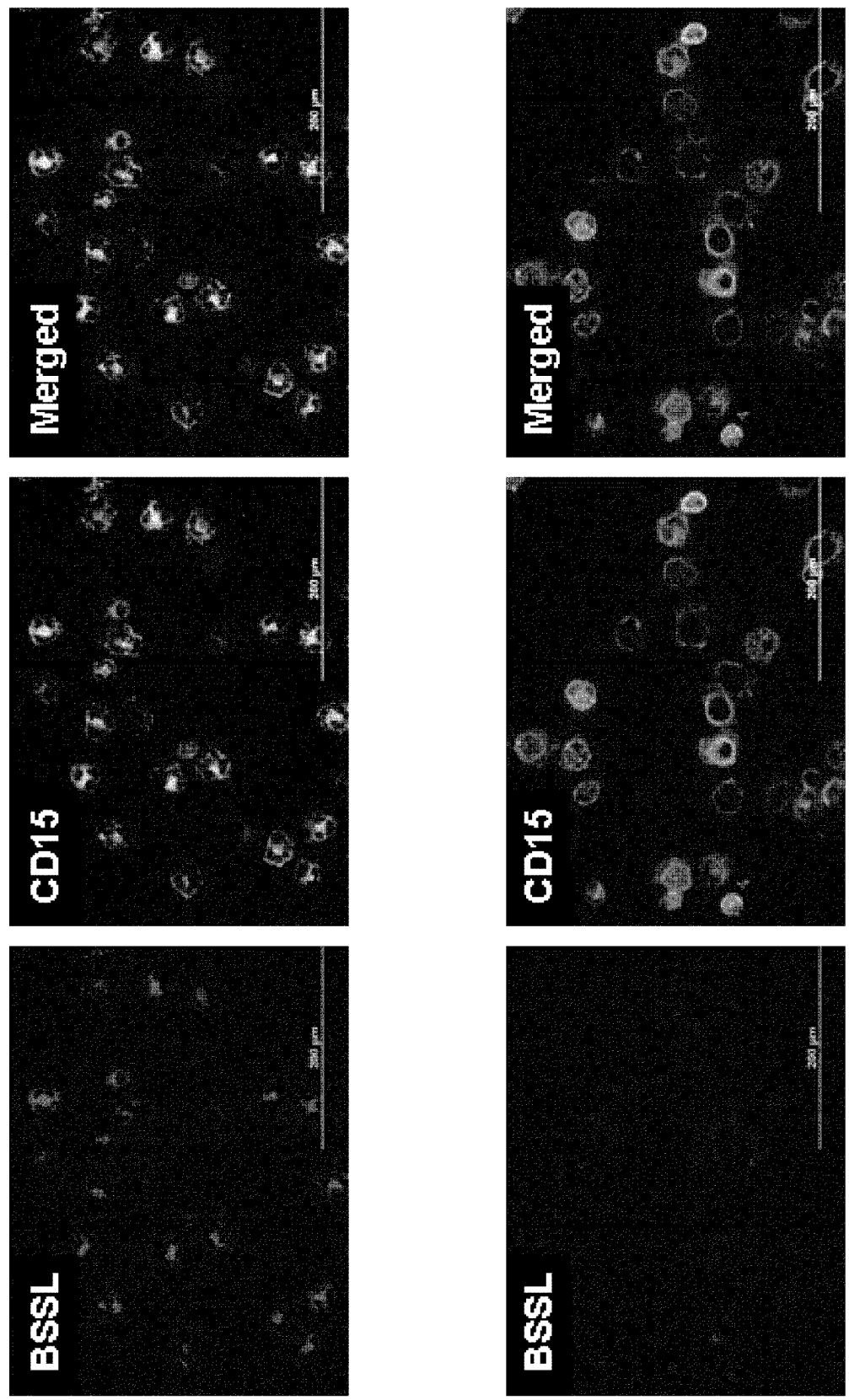

FIG. 6. Subcellular localization of BSSL in circulating granulocytes.

Human leukocytes were harvested from blood of healthy volunteers and stained by double immunofluorescence using rabbit polyclonal anti-BSSL and mouse monoclonal anti-CD15 antibodies. To distinguish between extracellular and intracellular localization, cells were either permeabilized (upper panel) or not (bottom panel) before antibodies were applied. A yellow color appeared in the merged picture in the upper panel, seen as bright staining in these black and white figures, indicating co-localization.

Figure 7:
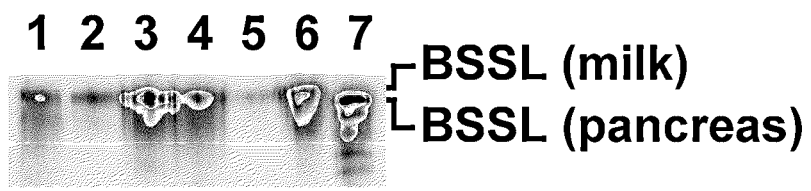

FIG. 7. Western blot analysis.

Affinity-purified protein extracts derived from human mononuclear blood cells (lanes 1 and 2) or polynuclear granulocytes (lanes 3-5) were separated by SDS-PAGE (10%), transferred to PVDF membranes, and probed with a polyclonal anti-human BSSL antibody. Protein extracts from human milk (lane 6) and human pancreas (lane 7) were used as positive controls.

Figure 8:
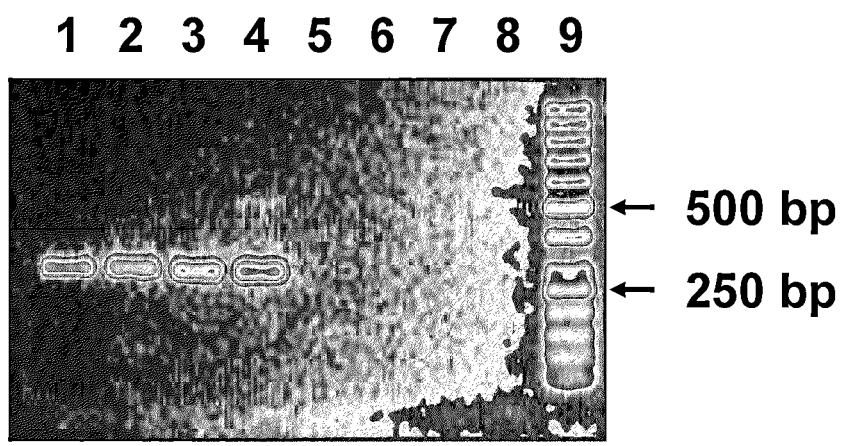

FIG. 8. Detection of BSSL mRNA in human blood cells.

Total RNA isolated from mononuclear blood cells and polynuclear granulocytes from two healthy individuals was reverse-transcribed and amplified using BSSL-specific oligonucleotide primers. The PCR products were resolved by 1.8% agarose gel electrophoresis and stained with ethidium bromide. A PCR product of the expected size (327 nt) was amplified from all samples. Mononuclear blood cells (lanes 1 and 2); polynuclear granulocytes (lanes 3 and 4). Negative controls (omitting RT from the cDNA synthesis reaction) are shown in lanes 5-8. The O'GeneRuler™ 50-bp DNA ladder (Fermentas) was used as a molecular size marker (lane 9).

Figure 9:
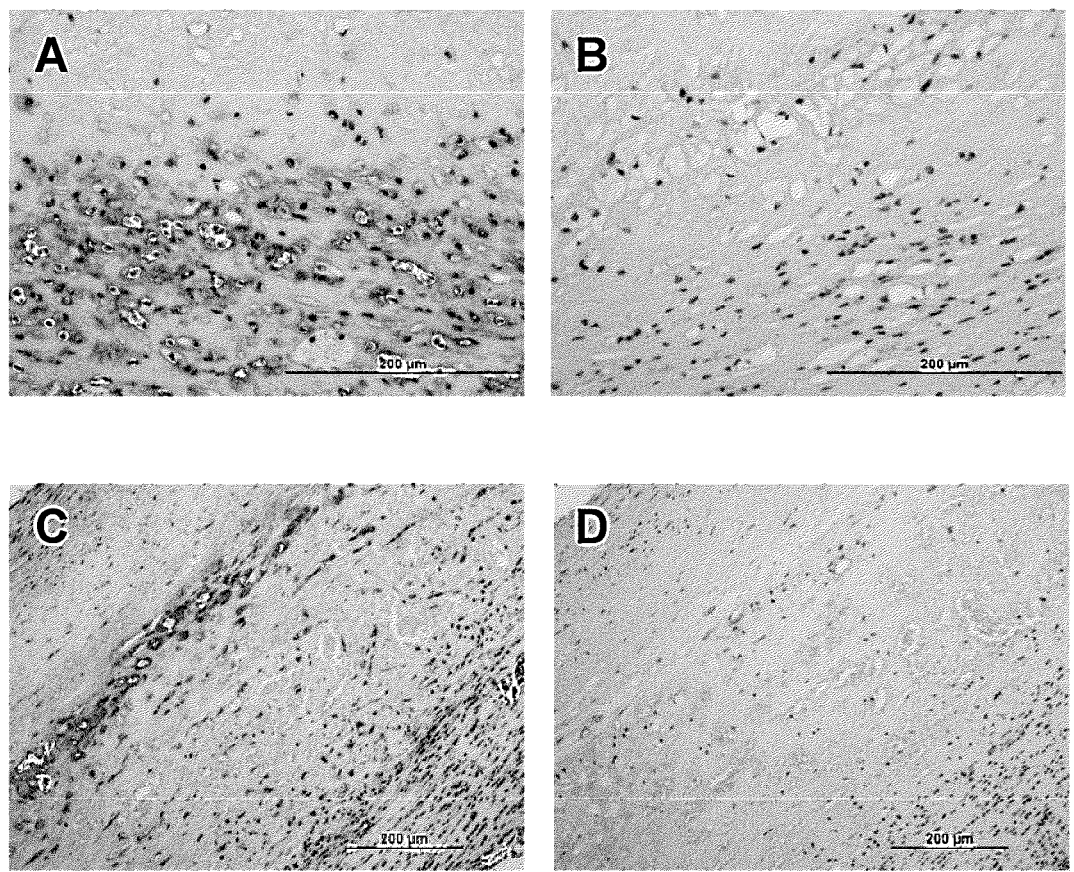

FIG. 9. Immunolocalization of BSSL in human atherosclerotic plaque.

Immunohistochemistry was performed on formalin-fixed, paraffin-embedded tissue sections obtained from atherosclerotic carotid arteries using a rabbit polyclonal BSSL-peptide (amino acid 328-341) antibody (A) and (C) or rabbit pre-immune serum (B) and (D), as negative control. Mayer's hematoxylin was used for counterstaining. The figure shows data from two patients (A, B are sections from patient 1; C, D are sections from patient 2).

Figure 10A:
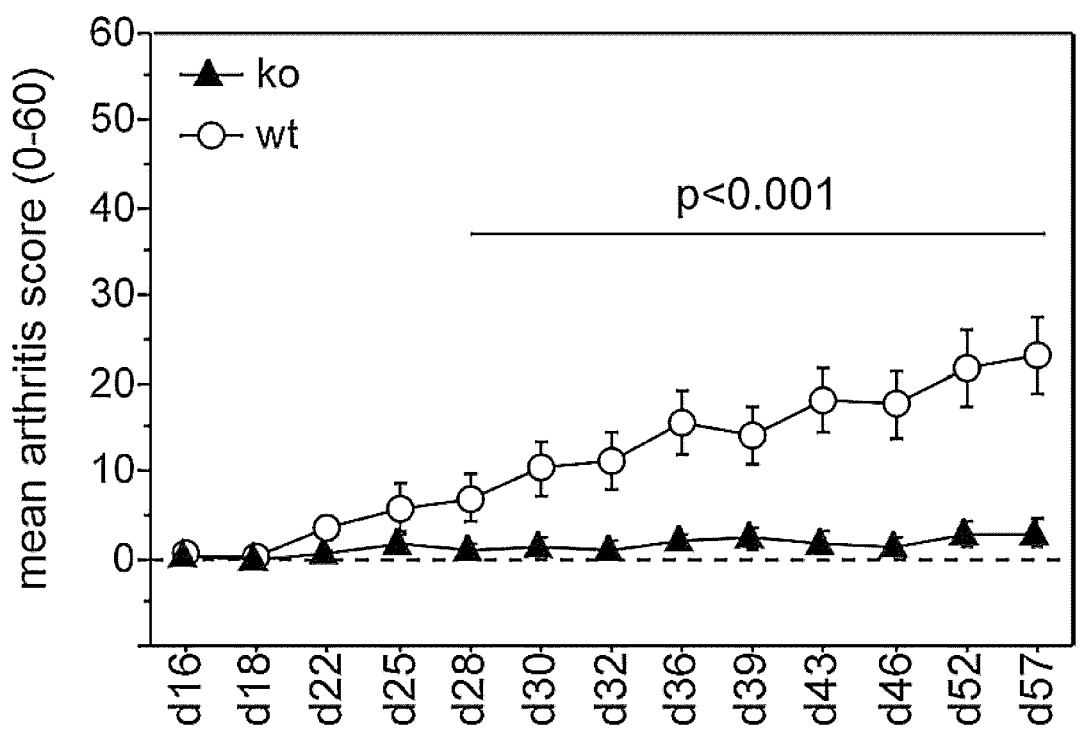
Figure 10B:
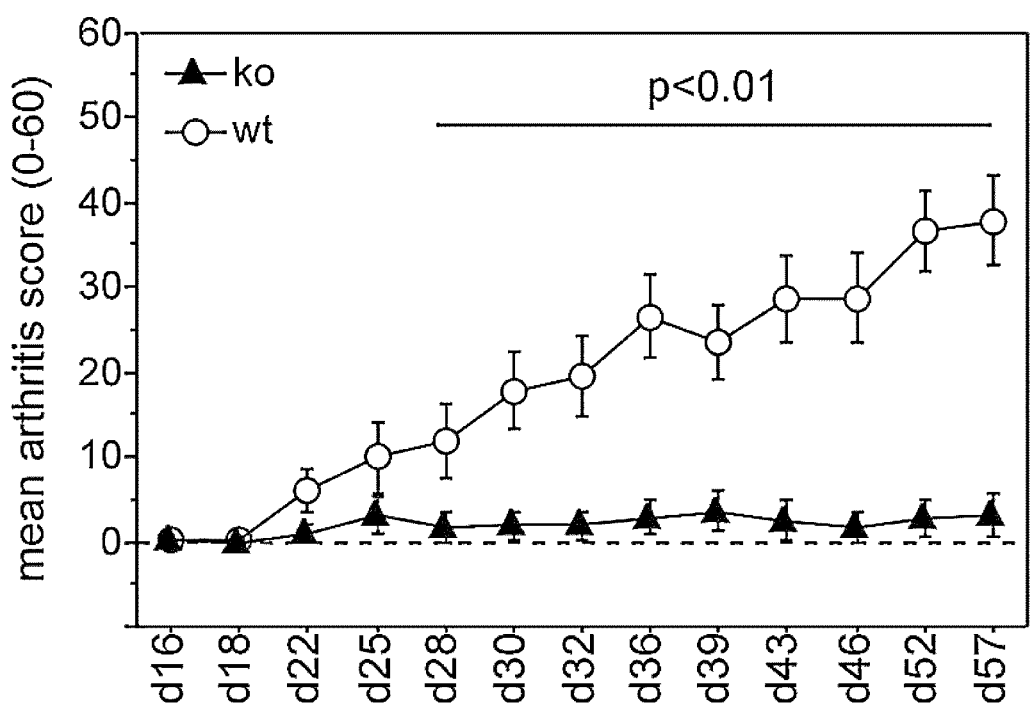
Figure 10C:
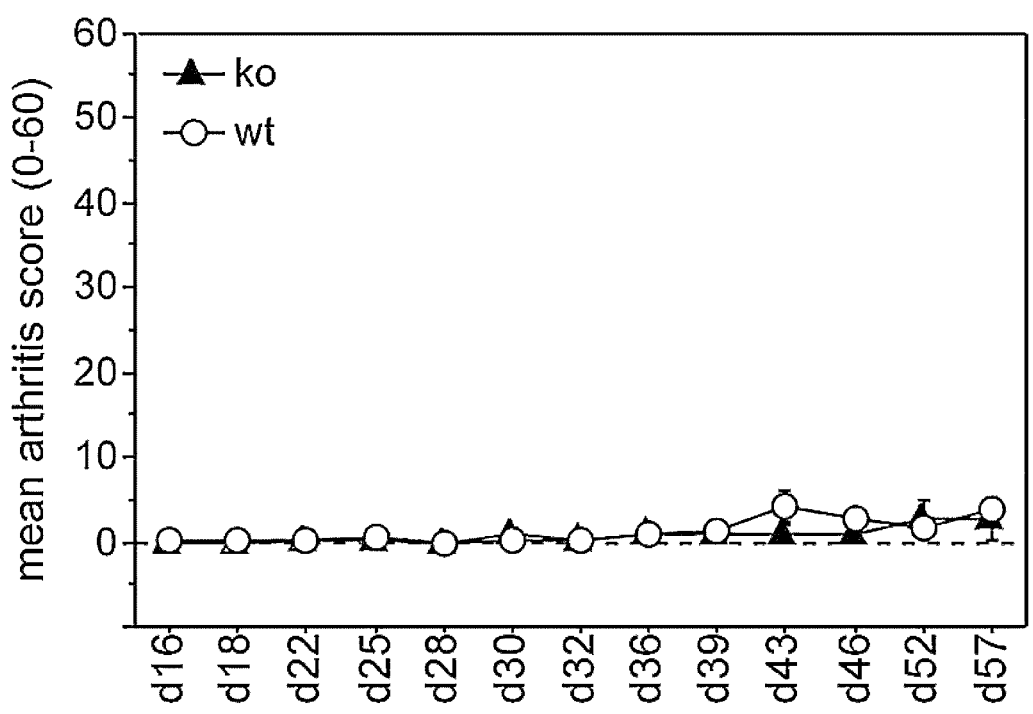

FIG. 10. Mean arthritis score in CIA mouse model.

Arthritis was followed for 57 days by scoring 2-3 times a week. BSSL deficient mice developed highly significantly lower disease score compared to wt controls. There was a profound difference in disease susceptibility between the sexes. Only few female mice developed arthritis and those who did had low score. (A) all mice; (B) males; (C) females.

Figure 11A:
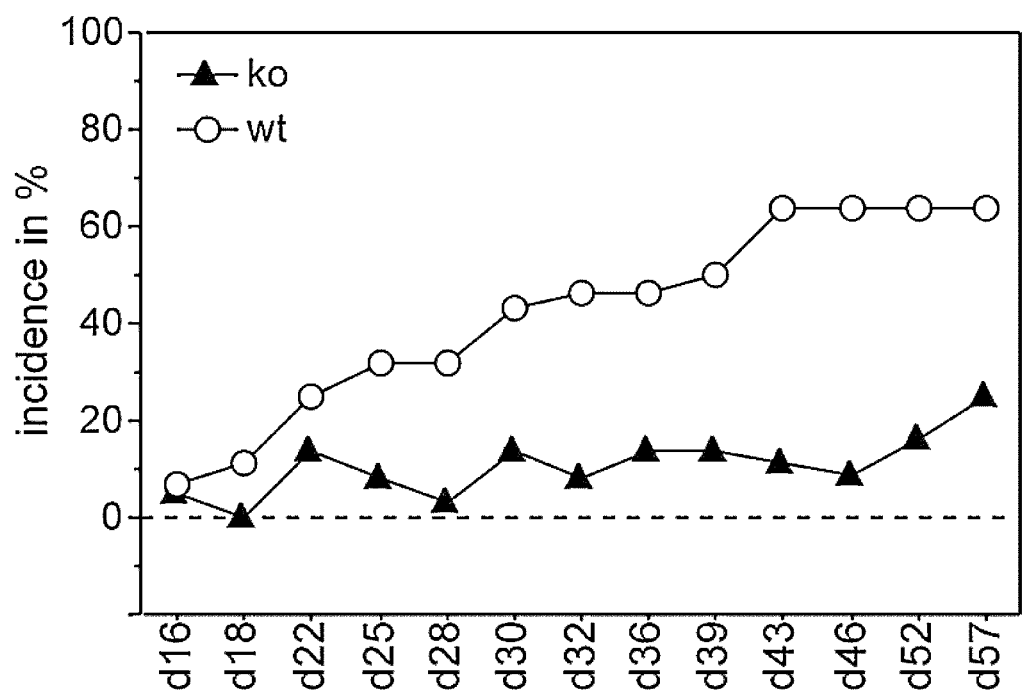
Figure 11B:
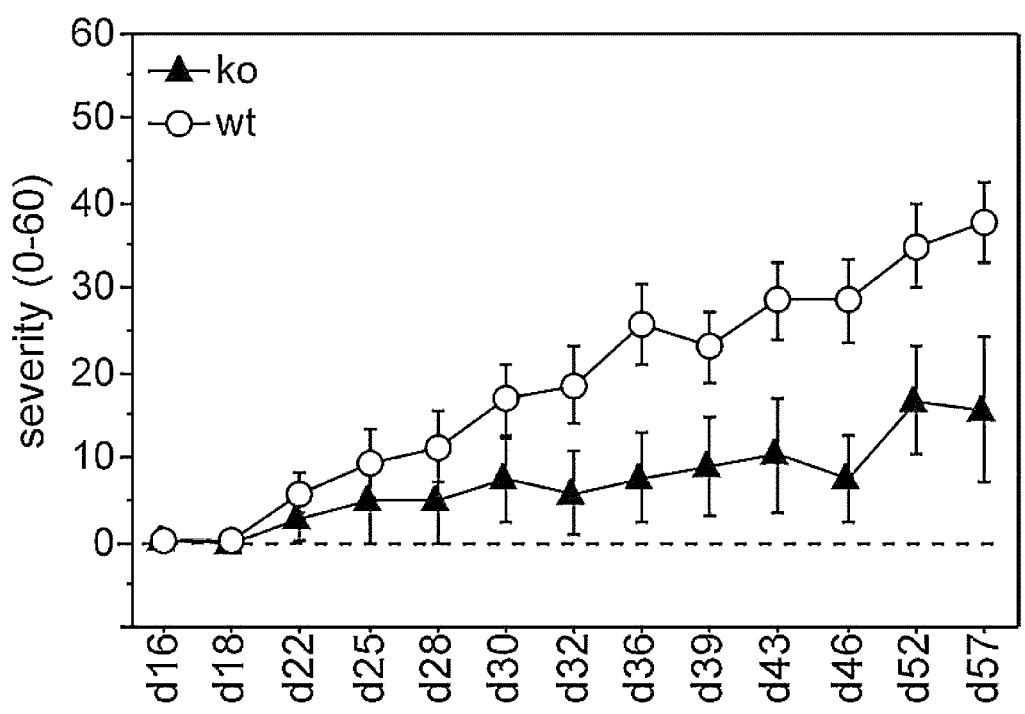

FIG. 11. Incidence and severity in CIA mouse model.

The BSSL deficient mice developed arthritis with reduced incidence and also lower severity compared to their wt littermates. Incidence is shown as percent of all mice (A) and severity is shown as mean arthritis score of sick mice only (B).

Figure 12A:
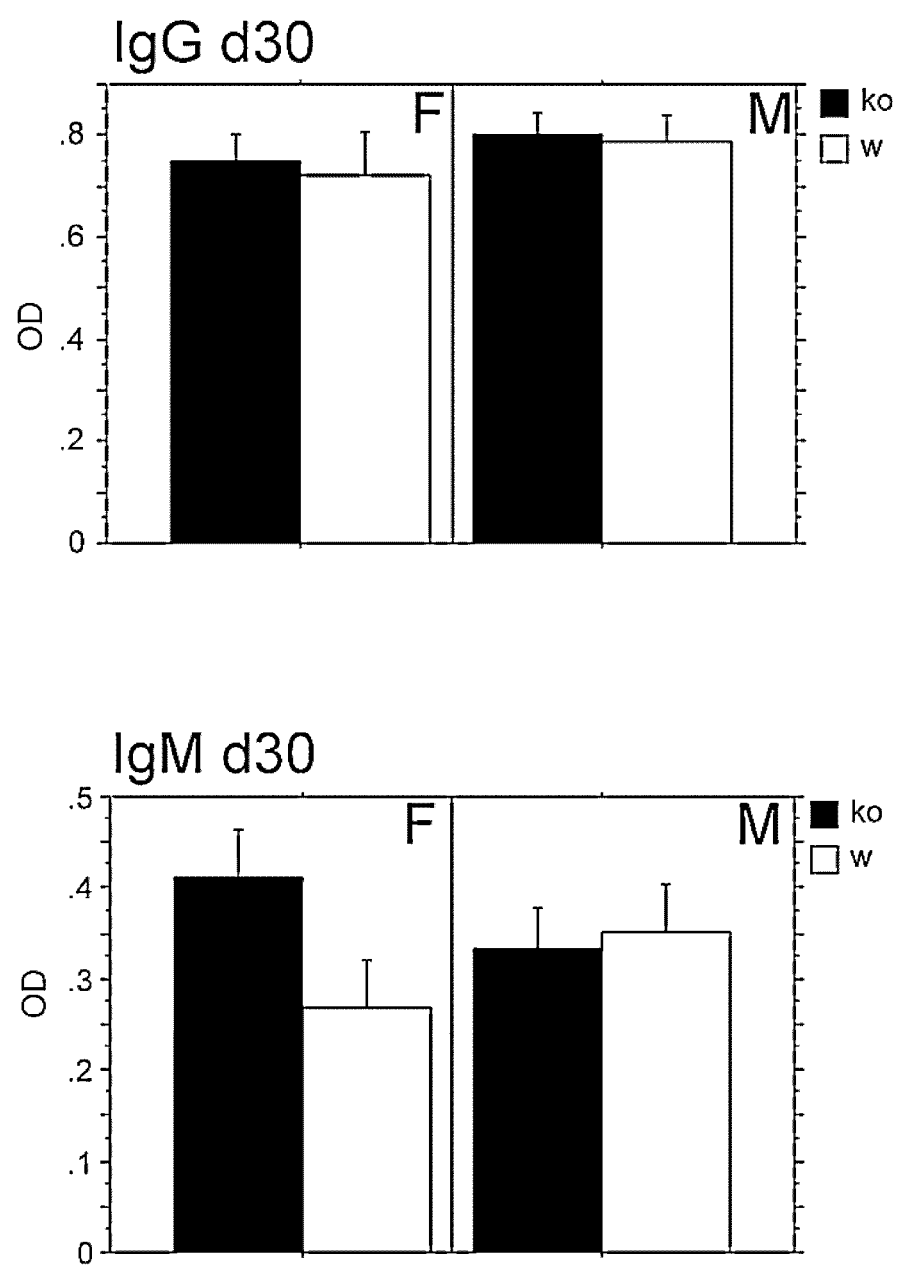
Figure 12B:
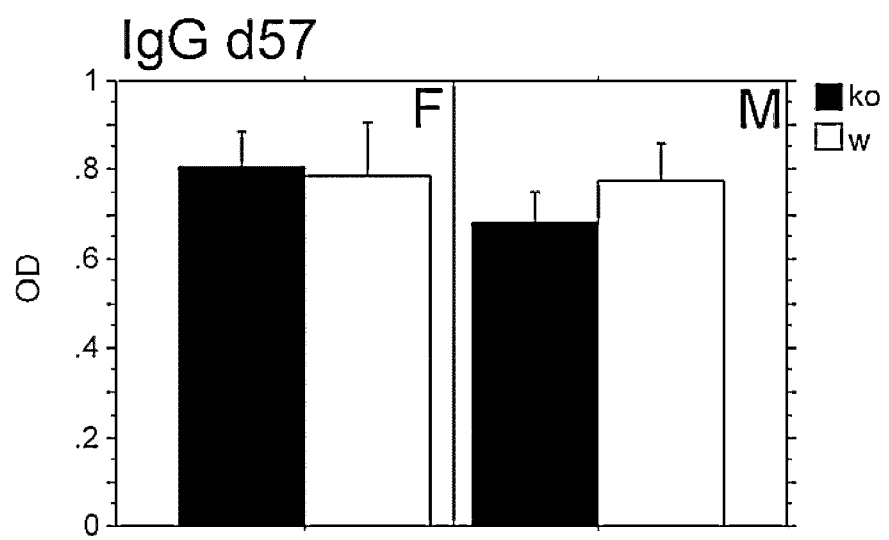
Figure 12B:
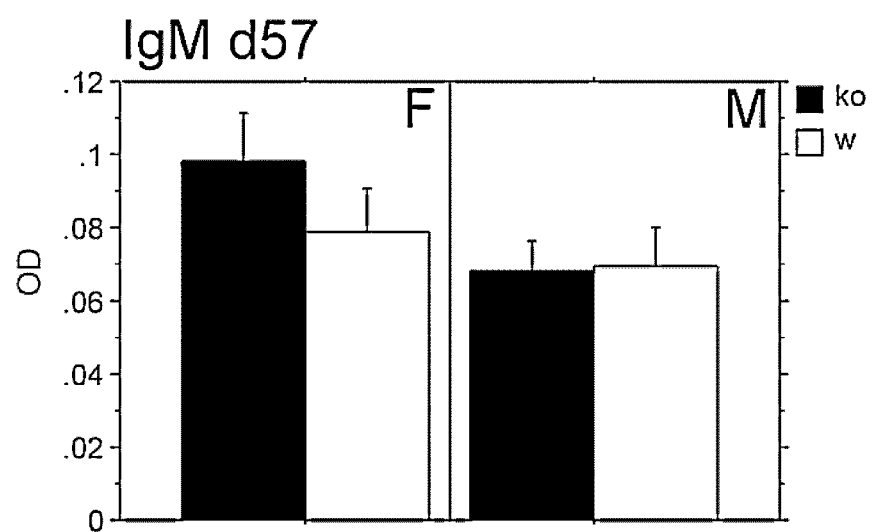

FIG. 12. Serum concentration of anti-CII antibodies in CIA mouse model.

Analysis of anti-collagen II (anti-CII antibody) concentration in serum withdrawn at day 30 (panel A) and day 57 (panel B) revealed no differences in response between BSSL deficient (black bars) and BSSL wt mice (white bars) in neither of the IgG isotypes (represented by total IgG in the figure), nor IgM.

Figure 13:
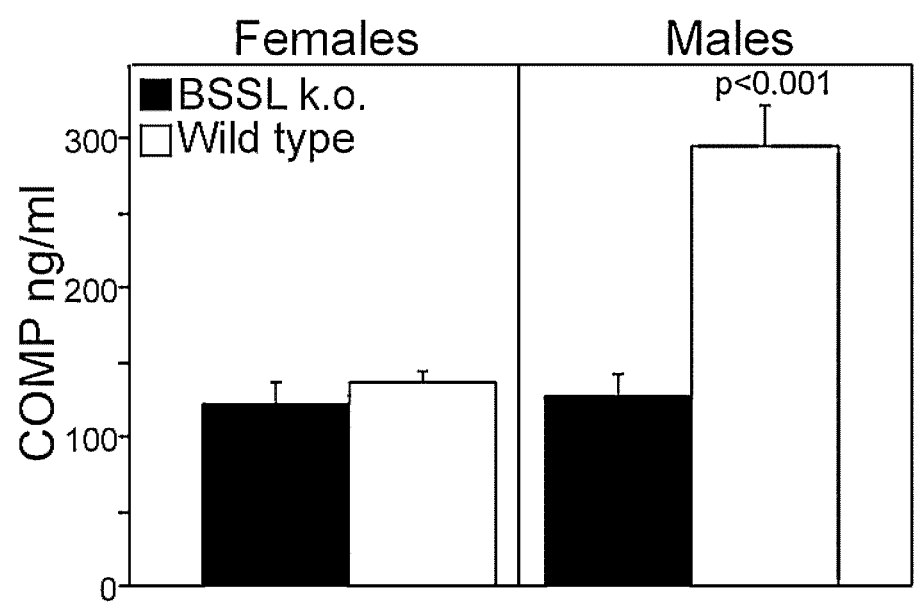

FIG. 13. Cartilage degradation in CIA mouse model.

The concentration of cartilage oligomeric matrix protein (COMP) in serum at day 57 was measured by ELISA as a marker for cartilage degradation. The level of COMP was significantly lower in BSSL deficient males (black bar) compared to wt male controls (white bar). In females there was no difference.

Figure 14A:
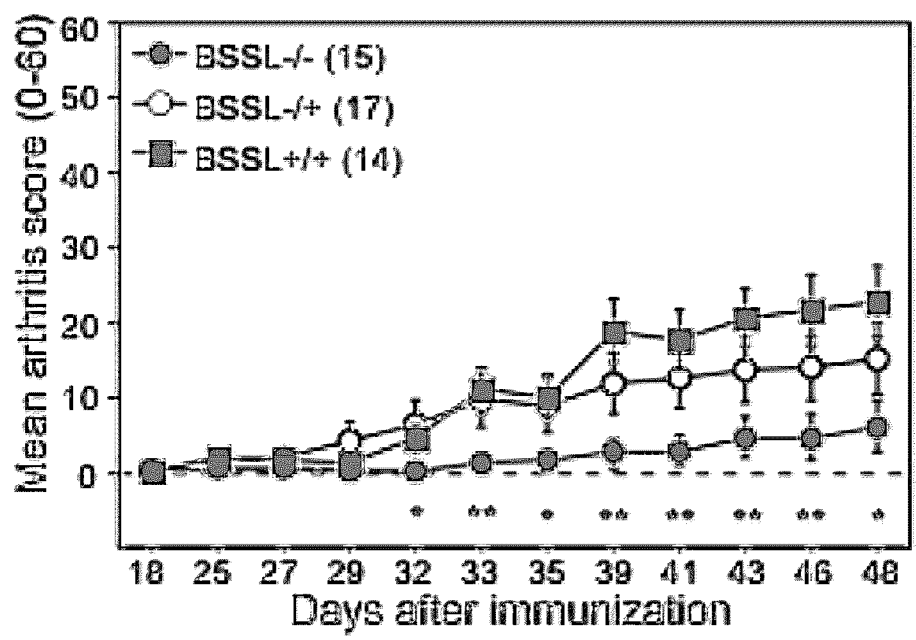
Figure 14B:
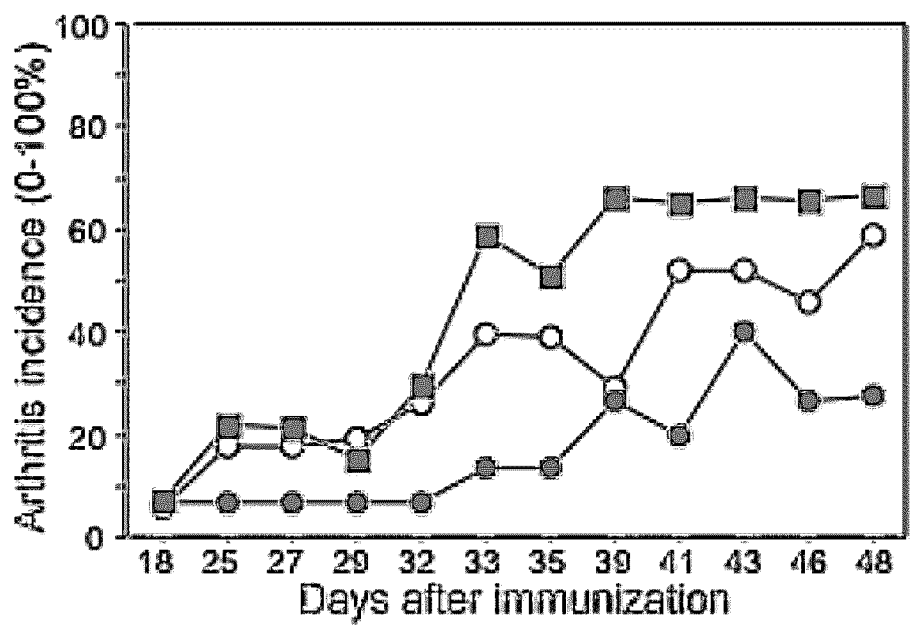
Figure 14C:
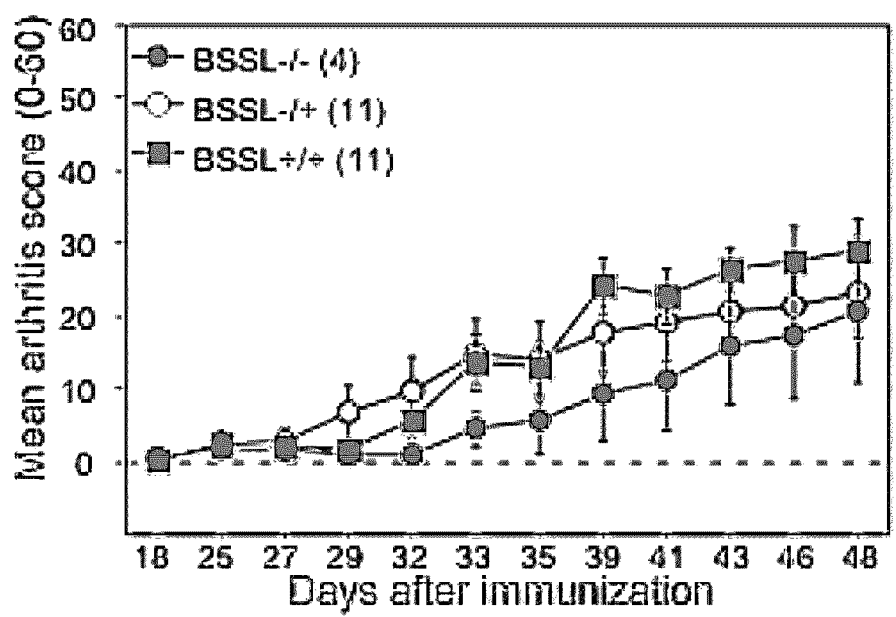

FIG. 14. Mean arthritis score, arthritis severity and incidence in CIA mouse model.

Arthritis was followed for 48 days by scoring 2-3 times a week. BSSL deficient mice showed a significantly lower disease score compared to BSSL wt mice (A) and (C), which was also reflected by a lower incidence of arthritis (B). BSSL heterozygous mice were less prone to develop disease as compared to BSSL wt mice but not as resistant as homozygous BSSL deficient mice. (A) and (B) all mice; (C) sick mice only. * represents $p<0.05$ and ** represents $p<0.01$.

Figure 15:
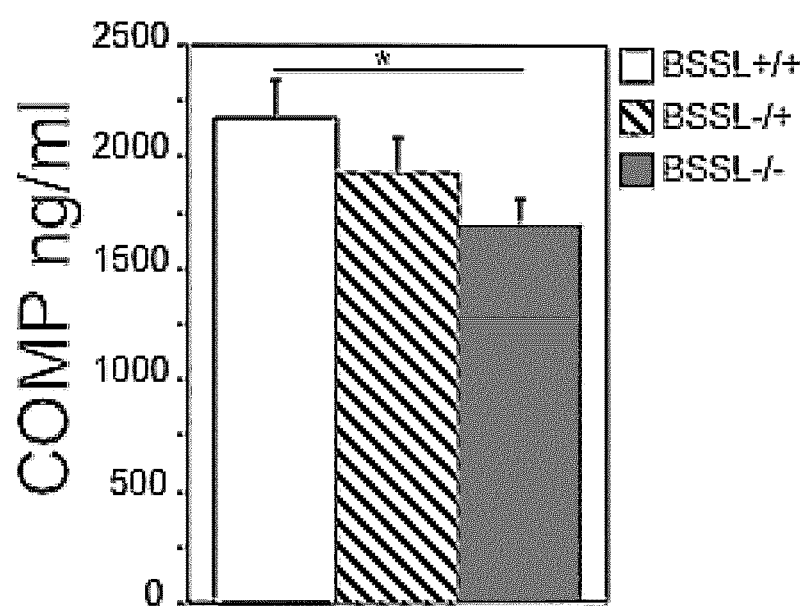

FIG. 15. Cartilage degradation in CIA mouse model.

The concentration of COMP in serum at day 48 was measured by ELISA as a marker for cartilage degradation. The level of COMP was significantly lower in BSSL deficient mice (black bar) compared to BSSL wt controls (white bar). The serum concentration of COMP in BSSL heterozygous mice (hatched bar) was found to be intermediate in relation to the concentration in BSSL deficient and BSSL wt mice. * represents $p<0.05$.

Figure 16:
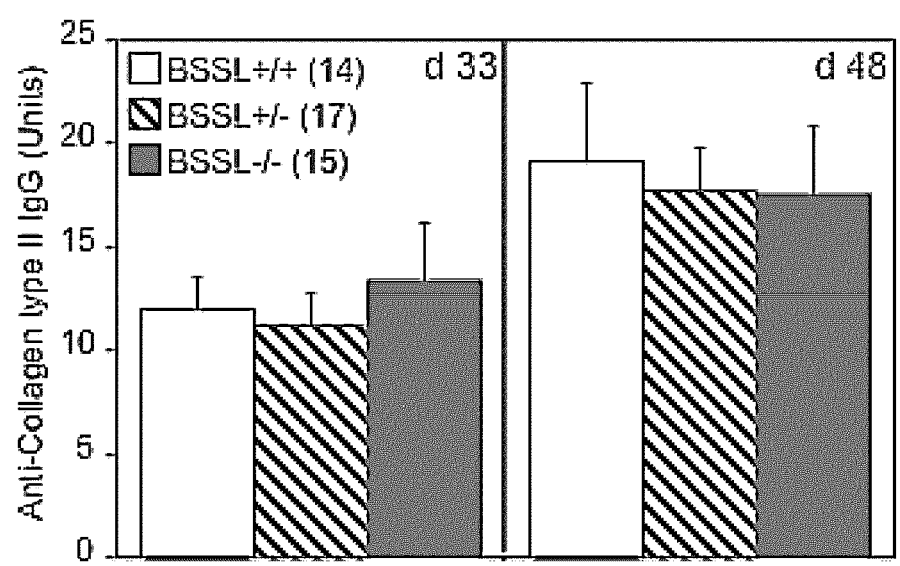

FIG. 16. Anti-collagen type II response (IgG) in plasma.

Analysis of anti-CII antibody levels at day 33 and day 48 presented as relative values compared to a standard of pooled serum. There was no significant difference in IgG response between any of the BSSL genotypes.

Figure 17:
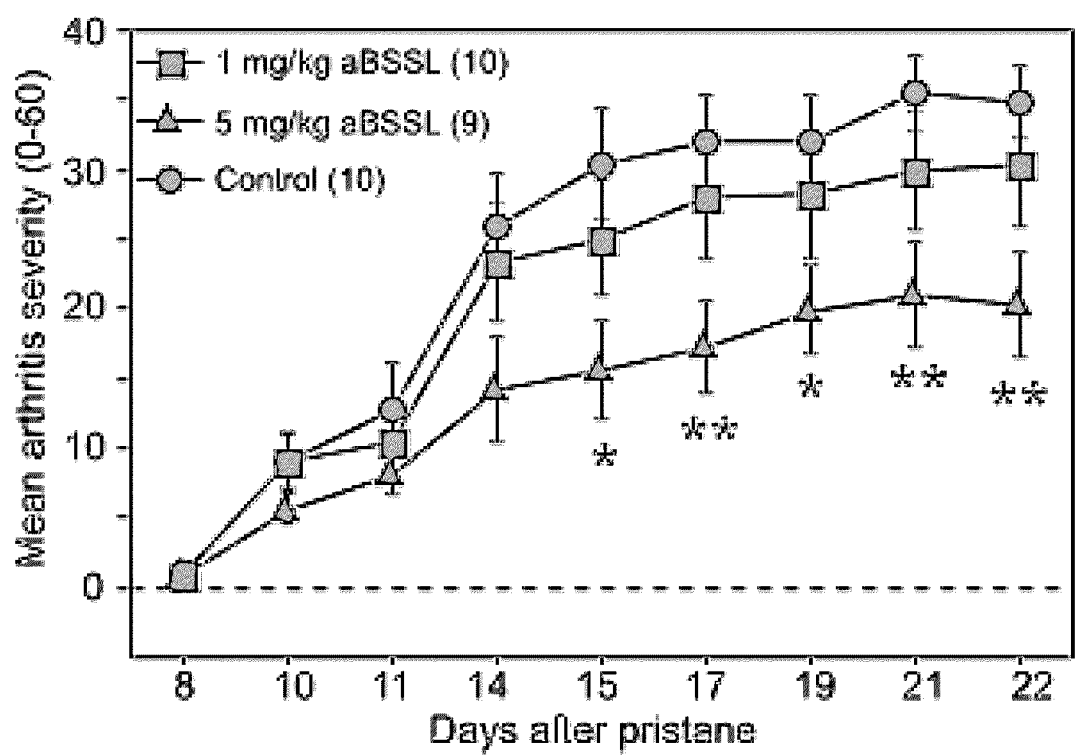

FIG. 17. Arthritis severity after anti-BSSL injections compared to control.

Rats injected with either 1 mg/kg or 5 mg/kg anti-BSSL showed significantly decreased disease severity. * represents p<0.05 and ** represents p<0.01. Incidence was 100% for all groups.

DETAILED DESCRIPTION OF THE INVENTION

The present invention is based on the discovery that BSSL has a role in inflammatory processes and that inhibition or elimination of BSSL protects from development of chronic arthritis in animal models. It is demonstrated that the BSSL protein is present in inflammatory cells and inflamed tissue. BSSL-deficient mice (BSSL-KO) developed collagen-induced arthritis (CIA) with significantly reduced disease severity and less incidence compared to wild-type controls. Injection of anti-BSSL antibodies significantly reduced disease severity of pristane-induced arthritis in rats.

The invention provides BSSL antagonists for the prevention and/or treatment of inflammatory diseases. Preferably, the BSSL antagonist can be an antibody or an antibody fragment specifically binding to human BSSL, or an RNAi molecule or an antisense polynucleotide comprising a sequence complementary to a part of a polynucleotide sequence encoding human BSSL.

Inflammatory Diseases

Inflammatory diseases that can be prevented and/or treated according to the invention are diseases selected from, but not limited to;

inflammatory diseases of the respiratory tract including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus;

inflammatory diseases of bone and joints including osteoarthritis/osteoarthrosis, both primary and secondary to, for example, congenital hip dysplasia; cervical and lumbar spondylitis, and low back and neck pain; rheumatoid arthritis and Still's disease; seronegative spondyloarthropathies including ankylosing spondylitis, psoriatic arthritis, reactive arthritis and undifferentiated spondarthropathy; septic arthritis and other infection-related arthropathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositis and polymyositis; polymyalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies;

inflammatory diseases related to connective tissue remodelling or musculoskeletal disorders due to injury (for example sports injury) or disease including arthritides (for example rheumatoid arthritis, osteoarthritis, gout or crystal arthropathy), other joint disease (such as intervertebral disc degeneration or temporomandibular joint degeneration), bone remodelling disease (such as osteoporosis, Paget's disease or osteonecrosis), polychondritis, scleroderma, mixed connective tissue disorder, spondyloarthropathies or periodontal disease (such as periodontitis);

inflammatory cardiovascular diseases including atherosclerosis, affecting the coronary and peripheral circulation; pericarditis; myocarditis, inflammatory and auto-immune cardiomyopathies including myocardial sarcoid; ischaemic reperfusion injuries; endocarditis, valvulitis, and aortitis including infective (for example syphilitic); vasculitides; disorders of the proximal and peripheral veins including phlebitis and thrombosis, including deep vein thrombosis and complications of varicose veins;

inflammatory disease of the skin including psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions;

inflammatory disease of the eyes including blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial;

inflammatory diseases of the gastrointestinal tract including glossitis, gingivitis, periodontitis; oesophagitis, including gastroesophageal reflux disease; eosinophilic gastro-enteritis, mastocytosis, coeliac disease, Crohn's disease, colitis, ulcerative colitis, proctitis, pruritis ani, irritable bowel disorder, irritable bowel syndrome, abdominal inflammatory diseases including hepatitis, including autoimmune, alcoholic and viral; fibrosis and cirrhosis of the liver; cholecystitis; pancreatitis, both acute and chronic;

genito-urinary tract inflammatory diseases including nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvovaginitis; Peyronie's disease; erectile dysfunction (both male and female);

allograft rejection including acute and chronic following, for example, transplantation of kidney, heart, liver, lung, bone marrow, skin or cornea or following blood transfusion; or chronic graft versus host disease;

inflammatory central nervous system diseases including Alzheimer's disease and other dementing disorders including Creutzfeldt-Jakob disease and New variant Creutzfeldt-Jakob disease; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, atypical facial pain, joint and bone pain, pain arising from cancer and tumor invasion, neuropathic pain syndromes including diabetic, post-herpetic, and HIV-associated neuropathies; neurosarcoidosis; central and peripheral nervous system complications of malignant, infectious or autoimmune processes; and other auto-immune and allergic disorders including Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome; other disorders with an inflammatory or immunological component; including acquired immune deficiency syndrome (AIDS), leprosy, Sezary syndrome, and paraneoplastic syndromes.

Preferably, the inflammatory disease that can be prevented and/or treated according to the invention is rheumatoid arthritis.

Antibodies

The term "antibody or antibody fragment" as referred to herein include whole antibodies and any antigen binding fragment referred to as "antigen-binding portion" or single chains thereof.

An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, $C_H1$, $C_H2$ and $C_H3$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding portion", as used herein, refers to one or more fragments of an antibody that retain the ability to specifically bind to an antigen (e.g. BSSL). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_H1$ domains; (ii) a F(ab')$_2$ fragment, a bivalent fragment comprising two Fab fragments linked by a disulfide bridge at the hinge region; (iii) a Fab' fragment, which is essentially an Fab with part of the hinge region; (iv) a Fd fragment consisting of the $V_H$ and $C_H1$ domains; (v) a Fv fragment consisting of the $V_L$ and $V_H$ domains of a single arm of an antibody, (vi) a dAb fragment (Ward et al. 1989) which consists of a $V_H$ domain; (vii) an isolated complementarity determining region (CDR); and (viii) a nanobody, a heavy chain variable region containing a single variable domain and two constant domains. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody," as used herein, is intended to refer to an antibody that is substantially free of other antibodies having different antigenic specificities (e.g., an isolated antibody that specifically binds BSSL is substantially free of antibodies that specifically bind antigens other than BSSL). An isolated antibody that specifically binds BSSL may, however, have cross-reactivity to other antigens, such as BSSL molecules from other species. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody," as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared there from (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and VL sequences, may not naturally exist within the human antibody germline repertoire in vivo.

As used herein, "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

The term "human antibody derivatives" refers to any modified form of the human antibody, e.g., a conjugate of the antibody and another agent or antibody.

The term "humanized antibody" is intended to refer to antibodies in which CDR sequences derived from the germline of another mammalian species, such as a mouse, have been grafted onto human framework sequences. Additional framework region modifications may be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

As used herein, an antibody that "specifically binding to human BSSL" is intended to refer to an antibody that binds to human BSSL with a $K_D$ of $1\times10^{-7}$ M or less, more preferably $5\times10^{-8}$ M or less, more preferably $3\times10^{-8}$ M or less, more preferably $1\times10^{-8}$ M or less, even more preferably $5\times10^{-9}$ M or less. The term "does not substantially bind" to a protein or cells, as used herein, means does not bind or does not bind with a high affinity to the protein or cells, i.e. binds to the protein or cells with a $K_D$ of $1\times10^{-6}$ M or more, more preferably $1\times10^{-5}$ M or more, more preferably $1\times10^{-4}$ M or more, more preferably $1\times10^{-3}$ M or more, even more preferably $1\times10^{-2}$ M or more.

The term "$K_{assoc}$" or "$K_a$," as used herein, is intended to refer to the association rate of a particular antibody-antigen interaction, whereas the term "$K_{dis}$" or "$K_d$," as used herein, is intended to refer to the dissociation rate of a particular antibody-antigen interaction. The term "$K_D$," as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore® system.

As used herein, the term "high affinity" for an IgG antibody refers to an antibody having a $K_D$ of $1\times10^{-7}$ M or less, more preferably $5\times10^{-8}$ M or less, even more preferably $1\times10^{-8}$ M or less, even more preferably $5\times10^{-9}$ M or less and even more preferably $1\times10^{-9}$ M or less for a target antigen. However, "high affinity" binding can vary for other antibody isotypes. For example, "high affinity" binding for an IgM isotype refers to an antibody having a $K_D$ of $10^{-6}$ M or less, more preferably $10^{-7}$ M or less, even more preferably $10^{-8}$ M or less.

As used herein, the term "subject" includes any human or nonhuman animal. The term "nonhuman animal" includes all vertebrates, e.g., mammals and non-mammals, such as non-human primates, sheep, dogs, cats, horses, cows, chickens, amphibians, reptiles, etc.

Anti-BSSL Antibodies

The antibodies to be used according to the invention are characterized by particular functional features or properties of the antibodies. For example, the antibodies bind specifically to human BSSL. Preferably, the antibodies bind to an epitope comprising an amino acid sequence present in the sequence of human BSSL (SEQ ID NO:2). Most preferably the antibodies bind to an epitope present in the amino acid sequence corresponding to amino acids 1 to 722 in SEQ ID NO:2, even more preferably the antibodies bind to an epitope present in the N-terminal part of BSSL, i.e. an epitope present in the amino acid sequence corresponding to amino acids 1 to 500 in SEQ ID NO:2.

Preferably, the antibody binds to human BSSL with high affinity, for example with a $K_D$ of $1\times10^7$ M or less. The anti-BSSL antibodies to be used according to the invention preferably exhibit one or more of the following characteristics:

(i) binds to human BSSL with a $K_D$ of $1\times10^{-7}$ M or less;
(ii) blocks the binding of BSSL to CXCR4 expressing cells;
(iii) blocks BSSL enhanced platelet aggregation;
(iv) blocks the binding of BSSL to the complex CXCR4/SDF-1
(v) blocks SDF-1 induced migration of leukocytes Preferably, the antibody binds to human BSSL with a $K_D$ of $5\times10^{-8}$ M or less, binds to human BSSL with a $K_D$ of $2\times10^{-8}$ M or less, binds to human BSSL with a $K_D$ of $5\times10^{-9}$ M or less, binds to human BSSL with a $K_D$ of $4\times10^{-9}$ M or less, binds to human BSSL with a $K_D$ of $3\times10^{-9}$ M or less, binds to human BSSL with a $K_D$ of $2\times10^{-9}$ M or less, or binds to human BSSL with a $K_D$ of $1\times10^{-9}$ M or less.

The antibody preferably binds to an antigenic epitope present in human BSSL, which epitope is not present in other proteins. The antibody typically binds to human BSSL but does not bind to other proteins, or binds to other proteins with a low affinity, such as with a $K_D$ of $1\times10^{-6}$ M or more preferably $1\times10^{-5}$ M or more, more preferably $1\times10^{-4}$ M or more, more preferably $1\times10^{-3}$ M or more, even more preferably $1\times10^{-2}$ M or more.

Standard assays to evaluate the binding ability of the antibodies toward human BSSL are known in the art, including for example, ELISAs, Western blots, RIAs, and flow cytometry analysis. The binding kinetics (e.g., binding affinity) of the antibodies also can be assessed by standard assays known in the art, such as by Biacore® system analysis.

Production of Monoclonal Antibodies

Monoclonal antibodies (mAbs) to be used according to the present invention can be produced by a variety of techniques, including conventional monoclonal antibody methodology e.g., the standard somatic cell hybridization technique of Kohler and Milstein (1975). Although somatic cell hybridization procedures are preferred, in principle, other techniques for producing monoclonal antibody can be employed e.g., viral or oncogenic transformation of B lymphocytes.

The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

Chimeric or humanized antibodies to be used according to the present invention can be prepared based on the sequence of a non-human monoclonal antibody prepared as described above. DNA encoding the heavy and light chain immunoglobulins can be obtained from the non-human hybridoma of interest and engineered to contain non-murine (e.g., human) immunoglobulin sequences using standard molecular biology techniques. For example, to create a chimeric antibody, murine variable regions can be linked to human constant regions using methods known in the art (see e.g., U.S. Pat. No. 4,816,567). To create a humanized antibody, murine CDR regions can be inserted into a human framework using methods known in the art (see e.g., U.S. Pat. No. 5,225,539).

In a preferred embodiment, the antibodies are human monoclonal antibodies. Such human monoclonal antibodies directed against BSSL can be generated using transgenic or transchromosomic mice carrying parts of the human immune system rather than the mouse system. These transgenic and transchromosomic mice include mice referred to herein as the HuMAb Mouse® and KM Mouse®), respectively, and are collectively referred to herein as "human Ig mice."

The HuMAb Mouse® (Medarex®, Inc.) contains human immunoglobulin gene miniloci that encode unrearranged human heavy (μ and γ) and κ light chain immunoglobulin sequences, together with targeted mutations that inactivate the endogenous μ and κ chain loci (see e.g., Lonberg et al. 1994). Accordingly, the mice exhibit reduced expression of mouse IgM or κ, and in response to immunization, the introduced human heavy and light chain transgenes undergo class switching and somatic mutation to generate high affinity human IgGκ monoclonal antibodies (Lonberg and Huszar 1995). See further, U.S. Pat. No. 5,545,806; and U.S. Pat. No. 5,770,429; U.S. Pat. No. 5,545,807; WO 92/03918, WO 93/12227, WO 94/25585, WO 97/13852, WO 98/24884, WO 99/45962, and WO 01/14424.

In another embodiment, human antibodies to be used according to the invention can be raised using a mouse that carries human immunoglobulin sequences on transgenes and transchromosomes, such as a mouse that carries a human heavy chain transgene and a human light chain transchromosome. This mouse is referred to herein as a "KM Mouse®," are described in detail in WO 02/43478.

Still further, alternative transgenic animal systems expressing human immunoglobulin genes are available in the art and can be used to raise anti-BSSL antibodies to be used according to the invention. For example, an alternative transgenic system referred to as the Xenomouse (Abgenix, Inc.) can be used; such mice are described in, for example, U.S. Pat. No. 5,939,598; U.S. Pat. No. 6,075,181; U.S. Pat. No. 6,114,598; U.S. Pat. No. 6,150,584 and U.S. Pat. No. 6,162,963. Moreover, alternative transchromosomic animal systems expressing human immunoglobulin genes are available in the art and can be used to raise anti-BSSL antibodies. For example, mice carrying both a human heavy chain transchromosome and a human light chain transchromosome, referred to as "TC mice" can be used; such mice are described in Tomizuka et al. (2000). Furthermore, cows carrying human heavy and light chain transchromosomes have been described in the art (Kuroiwa et al. 2002) and can be used to raise anti-BSSL antibodies.

Human monoclonal antibodies which can be used according to the invention can also be prepared using phage display methods for screening libraries of human immunoglobulin genes. Such phage display methods for isolating human antibodies are established in the art. See for example: U.S. Pat. No. 5,223,409; U.S. Pat. No. 5,403,484; U.S. Pat. No. 5,571,698; U.S. Pat. No. 5,427,908; U.S. Pat. No. 5,580,717; U.S. Pat. No. 5,969,108; U.S. Pat. No. 6,172,197; U.S. Pat. No. 5,885,793; U.S. Pat. No. 6,521,404; U.S. Pat. No. 6,544,731; U.S. Pat. No. 6,555,313; U.S. Pat. No. 6,582,915 and U.S. Pat. No. 6,593,081.

Human monoclonal antibodies can also be prepared using SCID mice into which human immune cells have been reconstituted such that a human antibody response can be generated upon immunization. Such mice are described in, for example, U.S. Pat. No. 5,476,996 and U.S. Pat. No. 5,698,767.

RNAi

RNAi molecules that can be used according to the invention comprises nucleotide sequences complementary to a part of a polynucleotide sequence selected from, a) the sequence SEQ ID NO:1,
b) a variant of SEQ ID NO:1 having at least 80%, preferably at least 90%, such as at least 95%, sequence identity to SEQ ID NO:1, and/or
c) a sequence complementary to the sequences a) and b).

Such RNAi molecules are potential BSSL antagonists.

Antisense

Antisense polynucleotides sequences that can be used according to the invention comprises nucleotide sequences complementary to a part of a polynucleotide sequence selected from, a) the sequence SEQ ID NO:1,
b) a variant of SEQ ID NO:1 having at least 80%, preferably at least 90%, such as at least 95%, sequence identity to SEQ ID NO:1, and/or
c) a sequence complementary to the sequences a) and b).

Such antisense polynucleotides sequences molecules are potential BSSL antagonists.

The percent sequence identity between two nucleic acid sequences is the number of positions in the sequence in which the nucleotide is identical, taking into account the number of gaps and the length of each gap, which need to be introduced for optimal alignment of the two sequences.

The percent identity between two polynucleotide sequences is determined as follows. First, a polynucleotide acid sequence is compared to, for example, SEQ ID NO:1 using the BLAST 2 Sequences (Bl2seq) program from the stand-alone version of BLASTZ containing BLASTN version 2.0.14 and BLASTP version 2.0.14. This stand-alone version of BLASTZ can be obtained from the U.S. Government's National Center for Biotechnology Information web site at http://www.ncbi.nlm.nih.gov. Instructions explaining how to use the Bl2seq program can be found in the readme file accompanying BLASTZ. Bl2seq performs a comparison between two polynucleotide sequences using the BLASTN algorithm. To compare two polynucleotide sequences, the options of Bl2seq are set as follows: -i is set to a file containing the first polynucleotide sequence to be compared (e.g., C:\seq1.txt); -j is set to a file containing the second polynucleotide sequence to be compared (e.g., C:\seq2.txt); -p is set to blastn; -o is set to any desired file name (e.g., C:\output.txt); and all other options are left at their default setting. For example, the following command can be used to generate an output file containing a comparison between two polynucleotide sequences: C:\Bl2seq -i c:\seq1.txt -j c:\seq2.txt -p blastn -o c:\output.txt. If the two compared sequences share sequence similarity, then the designated output file will present those regions of similarity as aligned sequences. If the two compared sequences do not share sequence similarity, then the designated output file will not present aligned sequences. Once aligned, the number of matches is determined by counting the number of positions where an identical nucleotide residue is presented in both sequences.

The percent identity is determined by dividing the number of matches by the length of the sequence set forth in an identified sequence followed by multiplying the resulting value by 100. For example, if a polynucleotide sequence of a length of 120 nucleotides is compared to the sequence set forth in SEQ ID NO:1 and the sequences once aligned as described above share a sequence where the number of matches is 114, then the sequence has a percent identity of 95% (i.e., 114÷120*100=95) to the sequence set forth in SEQ ID NO:1.

BSSL

Briefly, BSSL may be isolated from a suitable tissue such as milk. Alternatively recombinant BSSL can be produced using standard methods through the isolation of DNA encoding BSSL.

DNA encoding BSSL may be conveniently isolated from commercially available RNA, cDNA libraries, genomic DNA, or genomic DNA libraries using conventional molecular biology techniques such as library screening and/or Polymerase Chain Reaction (PCR). These techniques are extensively detailed in Molecular Cloning—A Laboratory Manual, $2^{nd}$ edition, Sambrook, Fritsch & Maniatis, Cold Spring Harbor Press.

The amino acid sequence of human BSSL can be obtained from the SwissProt database, accession no P19835 (CEL_HUMAN) (SEQ ID NO:2) and the cDNA sequence e.g. from the EMBL database accession no. X54457 (SEQ ID NO:1).

The resulting cDNAs encoding BSSL are then cloned into commercially available mammalian expression vectors such as the pcDNA3 (Invitrogen), pMClneo (Stratagene), pXT1 (Stratagene), pSGS (Stratagene), EBO-pSV2-neo (ATCC 37593), pBPV-1(8-2) (ATCC 37110), pdBPV-MMTneo (342-12) (ATCC 37224), pRSVgpt (ATCC 37199), pRSVneo (ATCC 37198), pSV2-dhfr (ATCC 37146), pUCTag (ATCC 37460), IZD35 (ATCC 37565), pLXIN, pSIR (Clontech), and pIRES-EGFP (Clontech). Standard transfection technologies are used to introduce the resulting expression vectors into commonly available cultured, mammalian cell lines such as L cells L-M(TK-) (ATCC CCL 1.3), L cells L-M (ATCC CCL 1.2), THP-1 (ATCC TIB 202), HEK 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C1271 (ATCC CRL 1616), BS-C-1 (ATCC CCL 26) and MRC-5 (ATCC CCL 171). CHO, HEK293, HeLa and clonal derivatives expressing the CEL are isolated. These transfected cell lines are used to produce recombinant CEL.

Alternatively the cDNAs encoding BSSL are cloned into commonly available expression vectors suitable for expression in micro organisms, such as bacterial expression vectors such as the pET (Invitrogen), pDEST (Invitrogen), pLEX (Invitrogen), pCAL (Stratagene); and the yeast expression vectors pYES (Invitrogen), pESC (Stratagene) for expression in *saccharomyces* and pPICZ (Invitrogen) for expression in *pichia*. Standard transfection technologies are used to introduce the resulting expression vectors into commonly available strains of micro organisms, such as the *E. coli* strains JM101 (Stratagene) and JM110 (Stratagene).

Methods for purification of BSSL from different tissues and transfected cell-lines are known in the art (Lombardo et al. 1978; Bläckberg and Hernell 1981; Wang and Johnson 1983; Hansson et al. 1993).

Formulation and Administration

The antibody and antibody fragments, RNAi molecules and antisense polynucleotides to be used according to this invention may be administered in standard manner for the condition that it is desired to treat, for example by oral, topical, parenteral, buccal, nasal, or rectal administration or by inhalation. For these purposes the antibodies and antibody fragments, RNAi molecules and antisense polynucleotides may be formulated by means known in the art into the form of, for example, tablets, capsules, aqueous or oily solutions, suspensions, emulsions, creams, ointments, gels, nasal sprays, suppositories, finely divided powders or aerosols for inhalation, and for parenteral use (including intravenous, intramuscular or infusion) sterile aqueous or oily solutions or suspensions or sterile emulsions.

Pharmaceutical compositions of the invention also can be administered in combination therapy, i.e., combined with other agents. For example, the combination therapy can include an anti-BSSL antibody combined with at least one other anti-inflammatory or immunosuppressant agent.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion).

The pharmaceutical composition of the invention may include one or more pharmaceutically acceptable salts. A "pharmaceutically acceptable salt" refers to a salt that retains the desired biological activity of the parent compound and does not impart any undesired toxicological effects (see e.g. Berge et al. 1977). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, monthly, once every 3 months or once every three to 6 months. Preferred dosage regimens for an anti-BSSL antibody according to the invention include 1 mg/kg body weight or 3 mg/kg body weight via intravenous, or subcutaneous, administration, or with the antibody being given using one of the following dosing schedules: (i) every four weeks for six dosages, then every three months; (ii) every three weeks; (iii) 3 mg/kg body weight once followed by 1 mg/kg body weight every three weeks.

EXAMPLES

Example 1

BSSL Appear in the Liver and Co-Localizes with Granulocytes at a State of Liver Steatosis The hypothesis that the liver could be a source for circulating BSSL was tested.

Subjects and Sample Acquisition

Human liver biopsies were obtained from four patients during elective abdominal surgery for carcinoma. The biopsies were taken from liver tissue at more than one centimeter distant from the site of the tumor. Patient 1 was a 62-year-old man who underwent surgery for colon cancer liver metastasis; patient 2 was a 73-year-old woman who underwent surgery for rectal cancer liver metastasis; patient 3 was a 60-year-old woman who underwent surgery for colon cancer liver metastasis, and patient 4 was a 63-year-old woman who underwent surgery for cholangiocellular carcinoma. All patients received general anesthesia.

Polymorphonuclear granulocytes and mononuclear cells were isolated from whole blood samples from healthy volunteers using the Polymorphprep™ (Axis-Shield PoC AS, Oslo, Norway), according to the manufacturer's guidelines.

Experimental protocols were approved by the Ethics Committee of the Medical Faculty of Umeå University, Sweden. Informed consent was obtained from all participants.

RNA Isolation, cDNA Synthesis, RT-PCR Amplification and Sequencing

Fresh liver specimens collected for RNA isolation were immediately submerged in TRIzol® Reagent (Invitrogen, Carlsbad, Calif., USA) and total RNA was isolated according to the manufacturer's instructions. Isolated human blood cells (polymorphonuclear granulocytes and mononuclear cells) were suspended in RNAlater® Solution (Ambion, Austin, Tex., USA) and incubated at 8° C. over night. Cells were pelleted, resuspended in TRIzol®, and total RNA was isolated according to the manufacturer's instructions. The RNA yield was quantified spectrophotometrically using a Nano-Drop® ND100 (NanoDrop Technologies, Wilmington, Del., USA) and the integrity of the RNA was assessed by ethidium bromide staining of ribosomal RNA bands separated on a 1% agarose gel. RNA samples were stored at −70° C. until use.

cDNA was generated from 1 µg of total RNA using random hexamers and TaqMan® reverse transcription reagents in a volume of 100 µl (Applied Biosystems®, Foster City, Calif., USA).

PCR was performed using AmpliTaq® Gold DNA polymerase (Applied Biosystems®) according to manufacturer's recommendations. One microliter of cDNA was amplified in a total volume of 20 Primer sequences were as follows: forward primer (BSSL10) 5'-TCCCGGGACCTGCCCGTTAT-5'(SEQ ID NO:3); reverse primer (BSSL 11) 5'-CTGCA-GAGAGACGCTGGCAC-3' (SEQ ID NO:4). PCR conditions were as follows: 95° C. for 5 min followed by 40 cycles of 94° C. for 45 s, 60° C. for 1 min, 72° C. for 1 min, and a final extension at 72° C. for 8 min. If the target sequence was present, the PCR reaction was expected to produce a 327-bp product, encompassing BSSL exons 4 and 5.

Direct sequencing of PCR fragments was performed using the Big Dye® Terminator v3.1 Cycle Sequencing Kit (Applied Biosystems®) according to manufacturer's recommendations. BSSL 10 or BSSL 11 (described above) was used as a primer. The reactions were analyzed using an ABI 3730XL DNA analyzer (Applied Biosystems®).

Protein Extraction and Western Blot Analysis

Pieces of liver tissue (approximately 100-200 mg) obtained from patients 2, 3, and 4 or blood cells (polynuclear granulocytes or mononuclear cells isolated from 10 ml of whole blood) were homogenized in a buffer containing protease inhibitors [0.047% $NH_3$, 0.4% Triton™ X-100, 0.08% sodium dodecyl sulfate (SDS), and 1 Mini Complete Tablet per 50 ml (Roche Diagnostics, Mannheim, Germany)]. The homogenate was centrifuged at 14,000 rpm for 10 min and the supernatant was collected and applied to a HiTrap™ NHS-activated column (GE Healthcare, Buckinghamshire, UK) coupled with anti-human BSSL polyclonal antibodies. The BSSL antibodies were raised in rabbits and purified as previously described (Hansson et al. 1993). After washing with phosphate buffered saline (PBS) supplemented with 0.02% sodium azide (NaN$_3$) and 0.01% ethylene diamine tetraacetic acid (EDTA), bound material was eluted by a buffer containing 0.1 M glycine (pH 2.5), 0.02% NaN$_3$ and 0.01% EDTA. All steps were performed at 4° C. to minimize the risk of proteolysis. Eluted proteins were separated on 10% SDS-polyacrylamide gel electrophoresis (PAGE) and transferred to polyvinylidene difluoride (PVDF) membranes (Bio-Rad, Hercules, Calif.). Western blotting was carried out using the ECL Advance Western Blotting Detection Kit, following the manufacturer's recommendations (GE Healthcare). A polyclonal anti-human BSSL antibody (Hansson et al. 1993) was used as primary antibody, and a peroxidase-conjugated donkey-anti-rabbit IgG (DAKO, Glostrup, Denmark) was used as secondary antibody. BSSL isolated from human milk (Bläckberg and Hernell 1981) and protein extracts from human pancreas were used as positive controls on the western blot.

Histological Analysis and Oil Red O Staining

Specimens for histological evaluation were fixed in 4% paraformaldehyde, 0.1 M phosphate buffer (pH 7.0) overnight, embedded in paraffin, microtome-sectioned, and stained with hematoxylin and eosin. For oil red O staining, tissues were fixed for 2 h at 4° C. in 4% paraformaldehyde, 0.1M phosphate buffer (pH 7.0), and cryoprotected by incubation over night in a solution of 30% sucrose in PBS at 4° C. Thereafter, the specimens were embedded in Tissue Tek® OCT™ compound (Sakura Finetek Europe B.V., Zoeterwoude, The Netherlands), frozen on dry ice, and stored at –70° C. until sectioning. Upon analysis, 8-μm thick sections were cut using a cryostat and mounted on SuperFrost™ Plus slides (Menzel-Gläser, Braunschweig, Germany). Sections were stained with oil red O staining solution (0.3% oil red O in 60% isopropyl alcohol) for 10 min at room temperature and then washed with 60% isopropyl alcohol.

Immunohistochemistry and Immunofluorescent Staining

Tissue samples were fixed, embedded, and cryosectioned as described above for oil red O staining. Isolated blood cells were applied in a drop of 10 μl onto SuperFrost Plus™ slides (Menzel-Gläser) and allowed to settle for 1 h at room temperature in a humidified chamber. The cells were washed in 3×PBS (2 min) and 1×PBS (2×2 min) and fixed in 4% paraformaldehyde, 0.1 M phosphate buffer (pH 7.0) for 20 min at room temperature.

For single staining-immunohistochemistry, air-dried sections were washed in Tris-buffered saline (TBS; 50 mM Tris-HCl, pH 7.5, 150 mM NaCl) for 3×5 min. Endogenous peroxidase activity was blocked by 20 min incubation in a solution of 80% methanol with 0.6% hydrogen peroxide (H$_2$O$_2$). After subsequent rinsing in TBS followed by TBS-T (TBS supplemented with 0.1% Triton X-100), sections were incubated with 10% normal horse serum (NHS) in TBS-T for 1 h. The first antibody (rabbit anti-BSSL, diluted 1:1000 in TBS-T+10% NHS) was applied and incubated for 2 h. After washing in TBS-T (3×5 min), the biotinylated secondary antibody was applied [goat anti-rabbit (Vector Laboratories Inc., Burlingame, Calif., USA), diluted 1:400 in TBS-T+10% NHS] and incubated for 1 h. Sections were washed in PBS (3×3 min) and incubated with Vectastain® Elite ABC Reagent (Vector Laboratories Inc.) for 1 h, washed again in PBS (3×3 min), and developed in diaminobenzidine (DAB) solution [1 tablet of DAB (10 mg) dissolved in 15 ml PBS+12 μl H$_2$O$_2$]. Finally, the sections were counterstained with Mayer's Hematoxylin, dehydrated, and mounted in DPX microscopy mounting medium (Merck Sharp & Dohme, Sweden). Negative controls comprised sections incubated with rabbit pre-immune serum instead of the primary antibody.

For immunofluorescence staining, air-dried liver sections or isolated blood cells, processed and mounted on SuperFrost™ Plus slides as above, were rinsed in PBS for 10 min. Endogenous peroxidase activity was blocked by incubation in 1% H$_2$O$_2$ for 10 min. After washing in PBS (3×3 min), sections or cells were incubated with 10% NHS in TBS-T for 1 h. Primary antibodies, diluted in TBS-T+10% NHS, were applied and incubated for 2 h. Sections or cells were washed in TBS-T (3×5 min). Secondary antibodies were applied (diluted 1:1000 in TBS-T+10% NHS), and the samples were incubated for 1 h. 4',6-diamidino-2-phenylindole (DAPI; Molecular Probes) was used for nuclear counterstaining. Sections or cells were washed in TBS-T (3×5 min) and mounted with Vectashield fluorescence medium. Negative controls were composed of sections or cells incubated with rabbit pre-immune serum instead of the primary antibody. For staining non-permeabilized cells, PBS replaced TBS-T in all steps. The main reactivities for all primary antibodies (apart from anti-BSSL) are summarized in Table 1.

TABLE 1

Co-localization of immune cell markers and BSSL in human liver

| Marker | Main reactivity | Dilution | Co-localize with BSSL |
|---|---|---|---|
| CD3 | Thymocytes, T cells | 1/100 | − |
| CD11b | Myeloid and NK cells | 1/50 | + |
| CD14 | Myelomonocytic cells | 1/100 | − |
| CD15 | Neutrophils, eosinophils, monocytes | 1/50 | + |
| CD19 | B cells | 1/50 | − |
| CD45 | All hematopoietic cells | 1/100 | + |
| CD56 | NK cells | 1/25 | − |
| CD57 | NK cells, subsets of T cells, B cells, and monocytes | 1/100 | − |
| CD68 | Monocytes, macrophages, neutrophils, basophils, large lymphocytes | 1/100 | − |
| CD86 | Monocytes, activated B cells, dendritic cells | 1/50 | − |
| HLA class II DR | Antigen presenting cells (B cells, monocytes, dendritic cells, T cells, granulocytes) | 1/50 | − |

The sources and clones were as follows: CD3, clone 289-13801 (Molecular Probes, Eugene, Oreg., USA); CD11b, clone 2LPM19C (DacoCytomation, Glostrup, Denmark); CD14, clone TUK4 (DacoCytomation); CD15, clone C3D-1 (DacoCytomation); CD19, clone HD37 (DacoCytomation); CD45, clone HI30 (BD Biosciences, San Jose, Calif., USA); CD56, clone T199 (DacoCytomation); CD57, clone NC1 (Immunotech, Marseilles, France); CD68, clone KP1 (DacoCytomation); CD86, clone FUN-1 (BD Biosciences); HLA class II DR, clone CR3/43 (DacoCytomation). The secondary antibodies used were Alexa Fluor® 488 goat-anti-rabbit, Alexa Fluor® 488 goat-anti-mouse, Alexa Fluor® 594 goat-ant-rabbit, and Alexa Fluor® 594 goat-anti-mouse (Molecular Probes).

Results

BSSL is Expressed in Human Liver Biopsies

Total RNA was extracted in duplicate from human liver biopsies collected from four patients (nos. 1-4). The RNA was reverse transcribed and amplified using BSSL-specific oligonucleotide primers designed to target exons 4-5. A PCR product corresponding to the expected size (327 nt) was amplified from all samples (FIG. 1). The 327-nt PCR fragments were sequenced and found to be identical to the published human BSSL cDNA sequence (EMBL accession no. X54457; data not shown).

Protein extracts were prepared from liver biopsies from patient no. 3 and no. 4 and applied to an anti-BSSL-sepharose column. After washing, the bound material was eluted and subjected to western analysis. A single protein with a molecular mass corresponding to the mass of human milk BSSL was detected in both samples (FIG. 2). The molecular mass of BSSL in the liver was comparable to that of BSSL found in human milk but slightly greater than the mass of the BSSL found in human pancreas.

Immunohistochemistry Localizes BSSL to Polynuclear Granulocytes in Human Liver

Hematoxylin-eosin and oil red O-staining of liver sections revealed that patient no. 4 suffered from extensive liver steatosis (FIGS. 3D and 3E). In contrast to patient no. 1 (FIGS. 3A and B), the entire section from patient no. 4 was crowded with large lipid-filled vacuoles. Immunohistochemistry using BSSL-specific antibodies on liver sections derived from patients 1 and 4 confirmed the presence of BSSL in human liver (FIGS. 3C and 3F). In sections from patient no. 4, cells that stained positive for BSSL seemed to cluster around the large lipid droplets (FIG. 3F), and the number of BSSL-positive cells was at least 10-fold higher in patient no. 4 than in patient no. 1. Moreover, cells that stained positive for BSSL in patient no. 1 did not cluster but were evenly scattered throughout the entire section (FIG. 3C). The BSSL-positive cells did not resemble hepatocytes morphologically, but instead resembled stellate cells or immune cells.

Figure 4A:
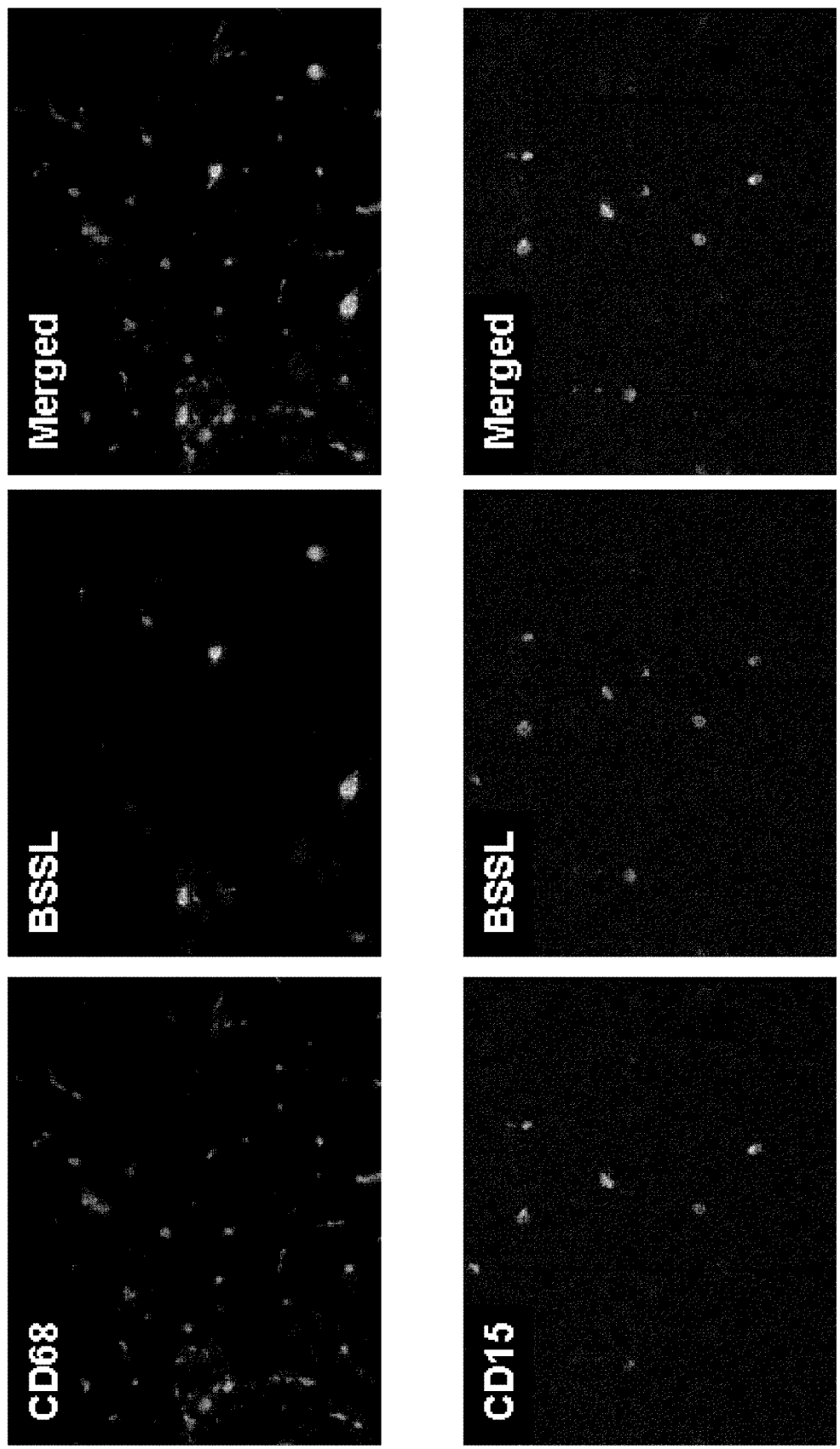
Figure 4B:
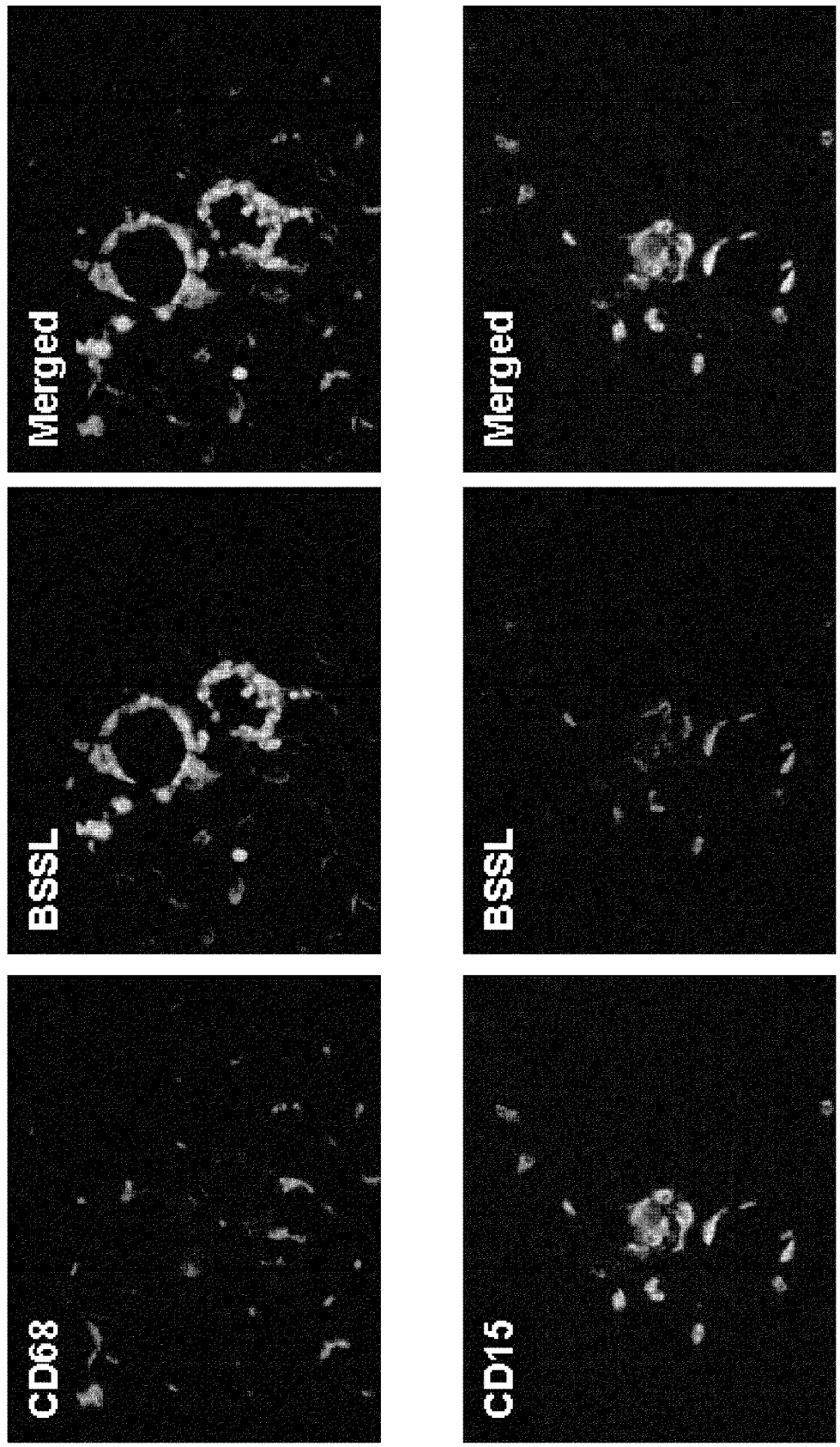

To investigate which cell type(s) expressed BSSL in human liver, double immunofluorescence staining was performed on tissue sections derived from patients no. 1 and no. 4. No co-localization was found between BSSL antibodies and antibodies directed toward smooth muscle actin or desmine, two antigens present on stellate cells (data not shown). In contrast, BSSL antibodies clearly co-localized with antibodies directed toward the leukocyte common antigen CD45, confirming that BSSL localized to immune cells (data not shown). To further investigate which cells expressed BSSL, we examined whether BSSL co-localized with different antigens present on a variety of immune cells (Table 1). Antibodies against CD3, CD14, CD19, CD56, CD57, CD86, and HLA class II DR all failed to co-localize with BSSL antibodies (data not shown), as did antibodies against CD68 (FIGS. 4A and 4B). However, anti-CD15 antibodies (present on 95% of mature granulocytes) and CD11b (present on myeloid cells and NK cells) clearly co-localized with BSSL-expressing cells (FIGS. 4A and 4B (CD15) and data not shown (CD11b)). These data showed that BSSL in human liver was not expressed by hepatocytes or other liver-specific cells, nor by macrophages as previously proposed, but most likely by granulocytes.

BSSL is Expressed by Circulating Blood Cells

Immunofluorescence studies revealed that BSSL and CD15 co-localized in permeabilized polymorphonuclear leukocytes isolated from whole human blood (FIG. 5). In contrast, anti-BSSL antibodies did not react to CD14-positive mononuclear cells (data not shown). Hence, in the circulation, BSSL was expressed by, or at least associated with, polymorphonuclear granulocytes. When immunofluorescence staining was performed on permeabilized and non-permeabilized granulocytes, BSSL-positive staining occurred only in permeabilized granulocytes (FIG. 6). In contrast, CD15 antibodies stained both permeabilized and non-permeabilized cells.

Polynuclear granulocytes and mononuclear cells were isolated separately from human blood. Protein extracts were generated from each cell population and applied to an anti-BSSL-sepharose column. Bound and eluted material was resolved by western immunoanalysis. Polyclonal anti-BSSL antibodies detected a single protein with a molecular mass corresponding to the mass of human milk BSSL in both polynuclear granulocytes and mononuclear cells (FIG. 7).

Total RNA isolated from polynuclear granulocytes and mononuclear blood cells was analyzed for the presence of BSSL mRNA by RT-PCR. A PCR product of the expected size (327 nt) was generated from both cell fractions (FIG. 8). Direct sequencing of the PCR fragments revealed a sequence identical to that of the published human BSSL cDNA (EMBL accession no. X54457; data not shown).

Example 2

BSSL is Present in Atherosclerotic Plaque

Histological Analysis and Immunohistochemistry

Specimens of human atherosclerotic carotid artery were fixed in 4% paraformaldehyde, 0.1 M phosphate buffer (pH 7.0) overnight, embedded in paraffin and microtome-sectioned. Immunohistochemistry was performed as described above. A polyclonal rabbit anti-human BSSL (directed against amino acid 328-341) was used as primary antibody in these experiments.

Results

The presence of BSSL in human atherosclerotic plaque was confirmed (FIG. 9). Taken together, the data presented above (Examples 1 and 2) suggest that BSSL, in addition to being a key enzyme in dietary fat digestion in early life, is also involved in inflammatory processes such as liver steatosis and atherosclerosis.

Example 3

BSSL Deficient Mice are Protected from Collagen Induced Arthritis (CIA)

Following the demonstration that BSSL is produced by granulocytes and platelets and present at the site of inflammation (liver steatosis and atherosclerotic plaques), the hypothesis that BSSL is involved in various conditions with inflammation as a common denominator, e.g. autoimmune arthritis was tested.

For this purpose the response of BSSL deficient "knockout" (BSSL-KO) mice was compared to wild-type mice in a collagen-induced arthritis (CIA) model (Courtenay et al. 1980). CIA is a commonly used experimental model in mice and rats that reproduces many of the pathogenic mechanisms of human rheumatoid arthritis (RA), i.e. increased cellular infiltration, synovial hyperplasia, pannus formation and erosion of cartilage and bone in the distal joints.

Study Design

BSSL-KO and BSSL-WT mice were immunized with collagen type II (CII) in complete Freunds adjuvant (CFA) day 0 and boosted with collagen type II (CII) in incomplete Freunds adjuvant (IFA) day 21, according to standard protocol. Severity of disease was followed for 57 days. Blood was taken day 30 and at the end of experiment (day 57).

Mice

To obtain susceptibility to CIA, conferred by the MHC $A^q$ haplotype, BSSL-KO mice of C57BL/6 background (gift from Dr. J. Breslow, Rockefeller University, New York) were crossed to the C57BL/10Q background for one generation (F1). BSSL heterozygous mice were then inter-crossed to generate BSSL-KO and BSSL-WT littermates, all carrying the MHC A$^q$ allele. These littermates were employed for the experiment.

Procedures

33 Males and 32 females from intercross generation F1 were used. The mice were bred and kept at 12 h light/dark cycles, in polystyrene cages containing wood shavings and were fed with standard rodent chow and water ad libitum at the animal house Umeå University. All mice included were either homozygous (n=26) or heterozygous (n=39) for the MHC A$^q$ haplotype allowing CII responsiveness (Wooley et al. 1981). In total 37 BSSL knock out (ko) and 28 wild type (wt) littermate mice were included in the experiment.

Mice were immunized with 100 μg rat CII in CFA, total volume of 50 μl at the base of the tail day 0. Emulgate was prepared in syringes using a connector (black) and kept on ice until use. A booster injection was performed day 21 with 50 μg rat CII in IFA (total volume 50 μl). Blinded clinical scoring of CIA was performed using a system based on the number of inflamed joints in each mouse. Inflammation was defined by the swelling and redness of the joints. Blood was taken by cheekbleeding day 30 and at the end of the experiment (day 57). The blood was taken in heparinised tubes and centrifuged to separate plasma (4,000 rpm, 10 min). Plasma was stored at −20° C. until assayed.

Plasma concentration of cartilage oligomeric matrix protein (COMP) was determined by a competitive ELISA according to an earlier described method (Saxne et al. 1992). Briefly, rat COMP was used for coating of the microtiter plates and for preparing the standard curve included in each plate. Plates were blocked with 1% bovine serum albumin (BSA) in PBS for 2 hours in room temperature. After blocking, plasma co-incubated with rabbit polyclonal antiserum against rat COMP (generously provided by Professor Dick Heinegård, Lund, Sweden) was added and the plates were incubated for 2 hours at room temperature. The amount of plasma COMP was estimated after incubation with an alkaline phosphatase-conjugated swine-anti-rabbit isotype-specific antibody (DAKO, Glostrup, Denmark) and phosphatase substrate (Sigma Aldrich) as substrate followed by detection in a Spectra Max® (Molecular Devices, Sunnyvale, Calif., USA) at OD 405 nm.

The antibody response against rat CII in plasma was determined with ELISA in 96-well plates (Costar, Camebridge, Mass. USA) coated overnight at 4° C. with 50 μl/well of 10 μg/ml rat CII in 50 μl PBS. All washes were performed with PBS (pH 7.4) containing 0.1% Tween®-20. Plasma was diluted in PBS and analyzed in duplicates. The amounts of bound IgG antibodies were estimated after incubation with biotin-conjugated isotype-specific antibodies (Southern Biotechnology Associates, Inc. Birmingham, Ala., USA) followed by Extravidin®-Peroxidase (Sigma) and developed with ABTS (Roche Diagnostics GmbH, Mannheim, Germany) as substrate followed by detection in a Spectra Max® at OD 405 nm (Molecular Devices).

Results

The results from the CIA experiment (FIGS. 10-13) show a significant protection from disease in mice that are knocked out for the BSSL gene. BSSL-KO mice develop arthritis with less incidence and lower severity (FIG. 11). The effect was mainly seen in males, but it is difficult to draw a conclusion on sex specificity since the females developed arthritis with too low incidence in general, and the disease developed with some delay relative to males. This was not surprising, since it is well known that male mice are more often affected than females in the CIA model. There was no difference in antibody response against CII (FIG. 13) but significantly less cartilage degradation in BSSL-KO mice which correlates with the arthritis development (FIG. 13).

Example 4

Collagen Induced Arthritis in BSSL-Deficient Mice (Follow-Up)

The CIA experiment described above was repeated with the same protocol and end-points (clinical scoring, anti-CII antibody response and COMP plasma concentration), but for this second CIA experiment BSSL heterozygote (BSSL-HET) mice were included and the study was limited to male mice. This follow-up study confirmed the results above and further showed that BSSL-HET mice were less prone to develop disease as compared to BSSL-WT mice but not as resistant as BSSL-KO mice (FIGS. 14-16).

Example 5

Pristane Induced Arthritis in Rats

It was hypothesized that antibodies directed towards BSSL could prevent binding of BSSL to its target and hence serve as therapeutic agents to block and/or ameliorate arthritis severity. To test this hypothesis in vivo, the effect of anti-BSSL antibodies was investigated in another animal model of autoimmune arthritis, i.e. pristane-induced arthritis (PIA) in rats.

Study Design

Dark Agouti (DA) rats, known to have a high susceptibility for developing PIA, were injected with pristane at day 0. At day 5, 10 and 15 the rats were injected with one of the following; 1) PBS, 2) anti-BSSL 1 mg/kg or 3) anti-BSSL 5 mg/kg) (n=10 for each group). Development of disease (arthritis severity) was followed by clinical scoring as described for the CIA model above.

Rats 40 male DA rats from Harlan Laboratories, Boxmeer, The Netherlands (8-10 weeks at arrival) were kept at 12 h light/dark cycles in polystyrene cages containing wood shavings and were fed with standard rodent chow and water ad libitum at the conventional animal house of BMC, Lund University, Lund. The experiment was approved by the Malmö/Lund ethical committee' under license number M107-07. One rat died during anesthesia during the experiment and was excluded. The rats were anesthetized for all injections.

Procedures

PIA was induced by s.c. injection at the base of the tail with 150 μl pristane day 0 using a 0.6×25 mm needle. Day 5, 10 and 15 rats were injected with either of the following treatments intraperitoneally (i.p.) in a total volume of 1 ml/rat a) PBS, b) polyclonal rabbit anti-human BSSL antibody (directed against amino acid 328-341) 1 mg/kg or c) anti-BSSL antibody 5 mg/kg (n=10 for each group). The rats were evaluated for arthritis severity from day 9 and until the end of experiment (day 22).

At the end of experiment, paws from representative rats were collected and fixed in 4% PFA, alternatively put in decalcifying EDTA solution. Fixed samples were moved to EDTA solution after 24 hours.

Results

The results from the PIA experiment showed that anti-BSSL antibodies (5 mg/kg) significantly reduced disease severity when injected at the initiation of disease (FIG. 17).

Even in the group injected with the lower dose (1 mg/kg) a tendency towards amelioration was found.

CONCLUSIONS

BSSL in Inflammatory Diseases

These present data demonstrate that BSSL, in addition to being a key enzyme in dietary fat digestion in early life, is present in granulocytes and involved in inflammatory processes. The present data further demonstrate that there is a requirement for BSSL in the inflammatory process and response in inflammatory diseases. Lack of BSSL or treatment with antibodies directed to BSSL significantly reduced disease severity in two animal models of rheumatoid arthritis.

REFERENCES

Aubert-Jousset E, Garmy N, Sbarra V, Fantini J, Sadoulet M and Lombardo D. 2004. The combinatorial extension method reveals a sphingolipid binding domain on pancreatic bile salt-dependent lipase: role in secretion. *Structure* 12(8): 1437-1447

Auge N, Rebai O, Lepetit-Thevenin J, Bruneau N, Thiers J C, Mas E, Lombardo D, Negre-Salvayre A, Verine A. 2003. Pancreatic bile salt-dependent lipase induces smooth muscle cells proliferation. *Circulation* 108:86-91

Bengtsson-Ellmark S, Nilsson J, Orho-Melander M, Dahlenborg K, Goop L and Bjursell, G. 2004. Association between a polymorphism in the carboxyl ester lipase gene and serum cholesterol profile. *European Journal of Human Genetics* 12: 627-632.

Berge S M, Bighley L D, Monkhouse D C. 1977. Pharmaceutical salts. *J. Pharm. Sci.* 66:1-19

Bird R E, Hardman K D, Jacobson J W, Johnson S, Kaufman B M, Lee S M, Lee T, Pope S H, Riordan G S, Whitlow M. 1988. Single-chain antigen-binding proteins. *Science* 242: 423-426

Bläckberg L, Blind P J, Ljungberg B, Hernell O. 1985. On the source of bile salt-stimulated lipase in human milk: a study based on serum concentrations as determined by sandwich enzyme-linked immunosorbent assay technique. *J Pediatr Gastroenterol Nutr* 4:441-445

Bläckberg, L and Hernell, O. 1981. The bile-salt-stimulated lipase in human milk. Purification and characterization. *Eur J Biochem* 116:221-225.

Bruneau N, Bendayan M, Gingras D, Ghitescu L, Levy E, Lombardo D. 2003. Circulating bile salt-dependent lipase originates from the pancreas via intestinal transcytosis. *Gastroenterology* 124:470-480

Bruneau N, Nganga A, Fisher E A and Lombardo D. 1997. O-Glycosylation of C-terminal tandem-repeated sequences regulates the secretion of rat pancreatic bile salt-dependent lipase. *J Biol Chem* 272:27353-27361.

Camarota, L M, Chapman, J M, Hui, D Y and Howles, P N. 2004. Carboxyl Ester Lipase Cofractionates with Scavenger Receptor BI in Hepatocyte Lipid Rafts and enhances Selective Uptake and Hydrolysis of Cholesteryl Esters from HDL3. *J. Biol. Chem.* 279: 27599-27606

Clemetson, K. J. et al. 2000. Functional expression of CCR1, CCR3, CCR4 and CXCR4 chemokine receptors on human platelets. *Blood* 96: 4046-4054.

Courtenay J S, Dallman M J, Dayan A D, Martin A, Mosedale B. 1980. Immunisation against heterologous type II collagen induces arthritis in mice. *Nature* 283:666-8.34.

Fält H, Hernell O, Blackberg L. 2002 Does bile salt-stimulated lipase affect cholesterol uptake when bound to rat intestinal mucosa in vitro? Pediatr Res; 52(4):509-15

Fayard E, Schoonjans K, Annicotte J S and Auwerx J. 2003. Liver receptor homolog 1 controls the expression of carboxyl ester lipase. *J Biol Chem* 278:35725-35731.

Gabriel S E. 2001. The epidemiology of rheumatoid arthritis. *Rheum Dis Clin North Am* 27:269-81

Hallett, M B, Williams, A S. 2008. Stopping the traffic: a route to arthritis therapy. *Eur J Immunol.* 38(10): 2650-2653.

Hansson L, Bläckberg L, Edlund M, Lundberg L, Strömqvist M and Hernell O. 1993. Recombinant human milk bile salt-stimulated lipase. Catalytic activity is retained in the absence of glycosylation and the unique proline-rich repeats. *J Biol Chem* 268:26692-26698.

Hernell O, Bläckberg L. 1997. Digestion and absorption of human milk lipids. In: Dulbecco R (ed) ENCYCLOPEDIA OF HUMAN BIOLOGY. Academic press, New York, pp 319-328

Howles P N, Carter C P and Hui D Y. 1996. Dietary free and esterified cholesterol absorption in cholesterol esterase (bile salt-stimulated lipase) gene-targeted mice. *J Biol Chem* 271:7196-7202.

Hui D Y. 1996. Molecular biology of enzymes involved with cholesterol ester hydrolysis in mammalian tissues. *Biochim. Biophys. Acta* 1303:1-14

Hui D Y, Howles P N. 2002. Carboxyl ester lipase: structure-function relationship and physiological role in lipoprotein metabolism and atherosclerosis. *J Lipid Res* 43:2017-2030

Kodvawala A, Ghering A B, Davidson W S, Hui D Y. 2005. Carboxyl ester lipase expression in macrophages increases cholesteryl ester accumulation and promotes atherosclerosis. *J Biol Chem* 280:38592-38598

Kohler, G and Milstein, C. 1975. Continuous cultures of fused cells secreting antibody of predefined specificity. *Nature* 256: 495-497.

Kuroiwa Y, Kasinathan P, Choi Y J, Naeem R, Tomizuka K, Sullivan E J, Knott J G, Duteau A, Goldsby R A, Osborne B A, Ishida I, Robl J M. 2002. Cloned transchromosomic calves producing human immunoglobulin. *Nature Biotechnology* 20:889-894

Lindquist S, Blackberg L and Hernell O. 2002. Human bile salt-stimulated lipase has a high frequency of size variation due to a hypervariable region in exon 11. *Eur J Biochem* 269:759-767.

Lindquist S, Hernell O. 2010. Lipid digestion and absorption in early life: an update. *Curr Opin Clin Nutr Metab Care.* (Epub ahead of print).

Lombardo, D, Guy, O, and Figarella, C. 1978. Purification and characterization of a carboxyl ester hydrolase from human pancreatic juice. *Biochim. Biophys. Acta* 527 (1): 142-149.

Lonberg N, Taylor L D, Harding F A, Trounstine M, Higgins K M, Schramm S R, Kuo C C, Mashayekh R, Wymore K, McCabe J G, et al. 1994 Antigen-specific human antibodies from mice comprising four distinct genetic modifications. *Nature* 368(6474): 856-859

Lonberg, N and Huszar, D. 1995. Human antibodies from transgenic mice. *Intern. Rev. Immunol.* 13: 65-93

Madeyski K, Lidberg U, Bjursell G and Nilsson J. 1999. Characterization of the gorilla carboxyl ester lipase locus, and the appearance of the carboxyl ester lipase pseudogene during primate evolution. *Gene* 239:273-282.

Naarding, M A, Dirac, A M, Ludwig, I S, Speijer, D, Lindquist, S, Vestman, E L, Stax, M J, Geijtenbeek, T B, Pollakis, G, Hernell, O, Paxton W A. 2006. Bile salt-stimulated lipase from human milk binds DC-SIGN and inhibits human immunodeficiency virus type 1 transfer to CD4+ T cells. *Antimicrob Agents Chemother.* 50(10): 3367-3374.

Nilsson J, Blackberg L, Carlsson P, Enerback S, Hernell O, Bjursell G. 1990. cDNA cloning of human-milk bile-salt-stimulated lipase and evidence for its identity to pancreatic carboxylic ester hydrolase. *Eur J Biochem* 192:543-550

Panicot-Dubois L. et al. 2007. Bile-salt-dependent lipase interacts with platelet CXCR4 and modulates thrombus formation in mice and humans. *Journal of Clinical Investigation* 117: 3708-3719.

Pentikainen M O, Oksjoki R, Oorni K, and Kovanen P T. 2002. Lipoprotein lipase in the arterial wall: linking LDL to the arterial extracellular matrix and much more. *Arterioscler Thromb Vasc Biol* 22:211-217

Ruvoen-Clouet N, Mas E, Marionneau S, Guillon P, Lombardo D, Le Pendu J. 2006. Bile-salt-stimulated lipase and mucins from milk of 'secretor' mothers inhibit the binding of Norwalk virus capsids to their carbohydrate ligands. *Biochemical J* 393 (Pt 3): 627-634.

Saxne, T and Heinegard, D. 1992. Cartilage oligomeric matrix protein: a novel marker of cartilage turnover detectable in synovial fluid and blood. *Br J Rheumatol* 31 (583-91.

Shamir R, Nganga A, Berkowitz D, Diamond E, Lischinsky S, Lombardo D, Shehadeh N. 2003. Serum levels of bile salt-stimulated lipase and breast feeding. *J Pediatr Endocrinol Metab* 16:1289-1294

Spilburg C A, Cox D G, Wang X, Bernat B A, Bosner M S, Lange L G. 1995. Identification of a species specific regulatory site in human pancreatic cholesterol esterase. *Biochemistry* 34(47): 15532-15538

Tomizuka K, Shinohara T, Yoshida H, Uejima H, Ohguma A, Tanaka S, Sato K, Oshimura M, Ishida I. 2000. Double trans-chromosomic mice: maintenance of two individual human chromosome fragments containing Ig heavy and kappa loci and expression of fully human antibodies. *Proc. Natl. Acad. Sci USA* 97:722-727

Wang C-S et al. 1995. Isolation and Characterization of Human Milk Bile Salt-Activated Lipase C-tail Fragment. *Biochemistry* 34(33): 10639-10644.

Wang, C S and Johnson, K. 1983. Purification of human milk bile salt-activated lipase. *Anal Biochem* 133 :457-461

Ward E S, Güssow D, Griffiths A D, Jones P T, Winter G, 1989 Binding activities of a repertoire of single immunoglobulin variable domains secreted from *Escherichia coli*. *Nature* 341:544-546

Wooley, P H, Luthra, H S, Stuart, J M, and. David, C S. 1981 Type II collagen-induced arthritis in mice. I. Major histocompatibility complex (I region) linkage and antibody correlates. *J Exp Med* 154, 688-700

What is claimed is:

1. A method for treating juvenile arthritis comprising administering a pharmaceutical effective amount of a BSSL antagonist comprising an antibody or an antibody fragment specifically binding to human bile salt-stimulated lipase (BSSL) to a subject in need of such treatment.

2. The method according to claim 1 wherein the antibody is a monoclonal antibody.

* * * * *

SEQUENCE LISTING

```
<160> NUMBER OF SEQ ID NOS: 4

<210> SEQ ID NO 1
<211> LENGTH: 2238
<212> TYPE: DNA
<213> ORGANISM: Homo sapiens
<220> FEATURE:
<221> NAME/KEY: CDS
<222> LOCATION: (1)..(2235)
<220> FEATURE:
<221> NAME/KEY: sig_peptide
<222> LOCATION: (1)..(69)
<220> FEATURE:
<221> NAME/KEY: mat_peptide
<222> LOCATION: (70)..(2235)

<400> SEQUENCE: 1 atg ctc acc atg ggg cgc ctg caa ctg gtt gtg ttg ggc ctc acc tgc      48
Met Leu Thr Met Gly Arg Leu Gln Leu Val Val Leu Gly Leu Thr Cys
            -20                 -15                 -10 tgc tgg gca gtg gcg agt gcc gcg aag ctg ggc gcc gtg tac aca gaa      96
Cys Trp Ala Val Ala Ser Ala Ala Lys Leu Gly Ala Val Tyr Thr Glu
         -5                  -1  1               5 ggt ggg ttc gtg gaa ggc gtc aat aag aag ctc ggc ctc ctg ggt gac     144
Gly Gly Phe Val Glu Gly Val Asn Lys Lys Leu Gly Leu Leu Gly Asp
 10                  15                  20                  25 tct gtg gac atc ttc aag ggc atc ccc ttc gca gct ccc acc aag gcc     192
Ser Val Asp Ile Phe Lys Gly Ile Pro Phe Ala Ala Pro Thr Lys Ala
                     30                  35                  40 ctg gaa aat cct cag cca cat cct ggc tgg caa ggg acc ctg aag gcc     240
Leu Glu Asn Pro Gln Pro His Pro Gly Trp Gln Gly Thr Leu Lys Ala
                 45                  50                  55 aag aac ttc aag aag aga tgc ctg cag gcc acc atc acc cag gac agc     288
Lys Asn Phe Lys Lys Arg Cys Leu Gln Ala Thr Ile Thr Gln Asp Ser
             60                  65                  70 acc tac ggg gat gaa gac tgc ctg tac ctc aac att tgg gtg ccc cag     336
Thr Tyr Gly Asp Glu Asp Cys Leu Tyr Leu Asn Ile Trp Val Pro Gln
         75                  80                  85
```

```
                                                        -continued ggc agg aag caa gtc tcc cgg gac ctg ccc gtt atg atc tgg atc tat       384
Gly Arg Lys Gln Val Ser Arg Asp Leu Pro Val Met Ile Trp Ile Tyr
90              95                  100                 105 gga ggc gcc ttc ctc atg ggg tcc ggc cat ggg gcc aac ttc ctc aac       432
Gly Gly Ala Phe Leu Met Gly Ser Gly His Gly Ala Asn Phe Leu Asn
                110                 115                 120 aac tac ctg tat gac ggc gag gag atc gcc aca cgc gga aac gtc atc       480
Asn Tyr Leu Tyr Asp Gly Glu Glu Ile Ala Thr Arg Gly Asn Val Ile
            125                 130                 135 gtg gtc acc ttc aac tac cgt gtc ggc ccc ctt ggg ttc ctc agc act       528
Val Val Thr Phe Asn Tyr Arg Val Gly Pro Leu Gly Phe Leu Ser Thr
        140                 145                 150 ggg gac gcc aat ctg cca ggt aac tat ggc ctt cgg gat cag cac atg       576
Gly Asp Ala Asn Leu Pro Gly Asn Tyr Gly Leu Arg Asp Gln His Met
    155                 160                 165 gcc att gct tgg gtg aag agg aat atc gcg gcc ttc ggg ggg gac ccc       624
Ala Ile Ala Trp Val Lys Arg Asn Ile Ala Ala Phe Gly Gly Asp Pro
170                 175                 180                 185 aac aac atc acg ctc ttc ggg gag tct gct gga ggt gcc agc gtc tct       672
Asn Asn Ile Thr Leu Phe Gly Glu Ser Ala Gly Gly Ala Ser Val Ser
                190                 195                 200 ctg cag acc ctc tcc ccc tac aac aag ggc ctc atc cgg cga gcc atc       720
Leu Gln Thr Leu Ser Pro Tyr Asn Lys Gly Leu Ile Arg Arg Ala Ile
            205                 210                 215 agc cag agc ggc gtg gcc ctg agt ccc tgg gtc atc cag aaa aac cca       768
Ser Gln Ser Gly Val Ala Leu Ser Pro Trp Val Ile Gln Lys Asn Pro
        220                 225                 230 ctc ttc tgg gcc aaa aag gtg gct gag aag gtg ggt tgc cct gtg ggt       816
Leu Phe Trp Ala Lys Lys Val Ala Glu Lys Val Gly Cys Pro Val Gly
    235                 240                 245 gat gcc gcc agg atg gcc cag tgt ctg aag gtt act gat ccc cga gcc       864
Asp Ala Ala Arg Met Ala Gln Cys Leu Lys Val Thr Asp Pro Arg Ala
250                 255                 260                 265 ctg acg ctg gcc tat aag gtg ccg ctg gca ggc ctg gag tac ccc atg       912
Leu Thr Leu Ala Tyr Lys Val Pro Leu Ala Gly Leu Glu Tyr Pro Met
                270                 275                 280 ctg cac tat gtg ggc ttc gtc cct gtc att gat gga gac ttc atc ccc       960
Leu His Tyr Val Gly Phe Val Pro Val Ile Asp Gly Asp Phe Ile Pro
            285                 290                 295 gct gac ccg atc aac ctg tac gcc aac gcc gcc gac atc gac tat ata      1008
Ala Asp Pro Ile Asn Leu Tyr Ala Asn Ala Ala Asp Ile Asp Tyr Ile
        300                 305                 310 gca ggc acc aac aac atg gac ggc cac atc ttc gcc agc atc gac atg      1056
Ala Gly Thr Asn Asn Met Asp Gly His Ile Phe Ala Ser Ile Asp Met
    315                 320                 325 cct gcc atc aac aag ggc aac aag aaa gtc acg gag gag gac ttc tac      1104
Pro Ala Ile Asn Lys Gly Asn Lys Lys Val Thr Glu Glu Asp Phe Tyr
330                 335                 340                 345 aag ctg gtc agt gag ttc aca atc acc aag ggg ctc aga ggc gcc aag      1152
Lys Leu Val Ser Glu Phe Thr Ile Thr Lys Gly Leu Arg Gly Ala Lys
                350                 355                 360 acg acc ttt gat gtc tac acc gag tcc tgg gcc cag gac cca tcc cag      1200
Thr Thr Phe Asp Val Tyr Thr Glu Ser Trp Ala Gln Asp Pro Ser Gln
            365                 370                 375 gag aat aag aag aag act gtg gtg gac ttt gag acc gat gtc ctc ttc      1248
Glu Asn Lys Lys Lys Thr Val Val Asp Phe Glu Thr Asp Val Leu Phe
        380                 385                 390 ctg gtg ccc acc gag att gcc cta gcc cag cac aga gcc aat gcc aag      1296
Leu Val Pro Thr Glu Ile Ala Leu Ala Gln His Arg Ala Asn Ala Lys
    395                 400                 405
```

-continued

```
agt gcc aag acc tac gcc tac ctg ttt tcc cat ccc tct cgg atg ccc    1344
Ser Ala Lys Thr Tyr Ala Tyr Leu Phe Ser His Pro Ser Arg Met Pro
410             415                 420                 425 gtc tac ccc aaa tgg gtg ggg gcc gac cat gca gat gac att cag tac    1392
Val Tyr Pro Lys Trp Val Gly Ala Asp His Ala Asp Asp Ile Gln Tyr
                430                 435                 440 gtt ttc ggg aag ccc ttc gcc acc ccc acg ggc tac cgg ccc caa gac    1440
Val Phe Gly Lys Pro Phe Ala Thr Pro Thr Gly Tyr Arg Pro Gln Asp
                    445                 450                 455 agg aca gtc tct aag gcc atg atc gcc tac tgg acc aac ttt gcc aaa    1488
Arg Thr Val Ser Lys Ala Met Ile Ala Tyr Trp Thr Asn Phe Ala Lys
        460                 465                 470 aca ggg gac ccc aac atg ggc gac tcg gct gtg ccc aca cac tgg gaa    1536
Thr Gly Asp Pro Asn Met Gly Asp Ser Ala Val Pro Thr His Trp Glu
    475                 480                 485 ccc tac act acg gaa aac agc ggc tac ctg gag atc acc aag aag atg    1584
Pro Tyr Thr Thr Glu Asn Ser Gly Tyr Leu Glu Ile Thr Lys Lys Met
490                 495                 500                 505 ggc agc agc tcc atg aag cgg agc ctg aga acc aac ttc ctg cgc tac    1632
Gly Ser Ser Ser Met Lys Arg Ser Leu Arg Thr Asn Phe Leu Arg Tyr
                    510                 515                 520 tgg acc ctc acc tat ctg gcg ctg ccc aca gtg acc gac cag gag gcc    1680
Trp Thr Leu Thr Tyr Leu Ala Leu Pro Thr Val Thr Asp Gln Glu Ala
                525                 530                 535 acc cct gtg ccc ccc aca ggg gac tcc gag gcc act ccc gtg ccc ccc    1728
Thr Pro Val Pro Pro Thr Gly Asp Ser Glu Ala Thr Pro Val Pro Pro
            540                 545                 550 acg ggt gac tcc gag acc gcc ccc gtg ccg ccc acg ggt gac tcc ggg    1776
Thr Gly Asp Ser Glu Thr Ala Pro Val Pro Pro Thr Gly Asp Ser Gly
        555                 560                 565 gcc ccc ccc gtg ccg ccc acg ggt gac tcc ggg gcc ccc ccc gtg ccg    1824
Ala Pro Pro Val Pro Pro Thr Gly Asp Ser Gly Ala Pro Pro Val Pro
570                 575                 580                 585 ccc acg ggt gac tcc ggg gcc ccc ccc gtg ccg ccc acg ggt gac tcc    1872
Pro Thr Gly Asp Ser Gly Ala Pro Pro Val Pro Pro Thr Gly Asp Ser
                    590                 595                 600 ggg gcc ccc ccc gtg ccg ccc acg ggt gac tcc ggg gcc ccc ccc gtg    1920
Gly Ala Pro Pro Val Pro Pro Thr Gly Asp Ser Gly Ala Pro Pro Val
                605                 610                 615 ccg ccc acg ggt gac tcc ggg gcc ccc ccc gtg ccg ccc acg ggt gac    1968
Pro Pro Thr Gly Asp Ser Gly Ala Pro Pro Val Pro Pro Thr Gly Asp
            620                 625                 630 tcc ggg gcc ccc ccc gtg ccg ccc acg ggt gac gcc ggg ccc ccc ccc    2016
Ser Gly Ala Pro Pro Val Pro Pro Thr Gly Asp Ala Gly Pro Pro Pro
        635                 640                 645 gtg ccg ccc acg ggt gac tcc ggc gcc ccc ccc gtg ccg ccc acg ggt    2064
Val Pro Pro Thr Gly Asp Ser Gly Ala Pro Pro Val Pro Pro Thr Gly
650                 655                 660                 665 gac tcc ggg gcc ccc ccc gtg acc ccc acg ggt gac tcc gag acc gcc    2112
Asp Ser Gly Ala Pro Pro Val Thr Pro Thr Gly Asp Ser Glu Thr Ala
                    670                 675                 680 ccc gtg ccg ccc acg ggt gac tcc ggg gcc ccc cct gtg ccc ccc acg    2160
Pro Val Pro Pro Thr Gly Asp Ser Gly Ala Pro Pro Val Pro Pro Thr
                685                 690                 695 ggt gac tct gag gct gcc cct gtg ccc ccc aca gat gac tcc aag gaa    2208
Gly Asp Ser Glu Ala Ala Pro Val Pro Pro Thr Asp Asp Ser Lys Glu
            700                 705                 710 gct cag atg cct gca gtc att agg ttt tag                            2238
Ala Gln Met Pro Ala Val Ile Arg Phe
        715                 720
```

```
<210> SEQ ID NO 2
<211> LENGTH: 745
<212> TYPE: PRT
<213> ORGANISM: Homo sapiens

<400> SEQUENCE: 2

Met Leu Thr Met Gly Arg Leu Gln Leu Val Val Leu Gly Leu Thr Cys
            -20                 -15                 -10

Cys Trp Ala Val Ala Ser Ala Ala Lys Leu Gly Ala Val Tyr Thr Glu
         -5              -1   1                   5

Gly Gly Phe Val Glu Gly Val Asn Lys Lys Leu Gly Leu Leu Gly Asp
 10                  15                  20                  25

Ser Val Asp Ile Phe Lys Gly Ile Pro Phe Ala Ala Pro Thr Lys Ala
                 30                  35                  40

Leu Glu Asn Pro Gln Pro His Pro Gly Trp Gln Gly Thr Leu Lys Ala
                 45                  50                  55

Lys Asn Phe Lys Lys Arg Cys Leu Gln Ala Thr Ile Thr Gln Asp Ser
                 60                  65                  70

Thr Tyr Gly Asp Glu Asp Cys Leu Tyr Leu Asn Ile Trp Val Pro Gln
     75                  80                  85

Gly Arg Lys Gln Val Ser Arg Asp Leu Pro Val Met Ile Trp Ile Tyr
 90                  95                  100                 105

Gly Gly Ala Phe Leu Met Gly Ser Gly His Gly Ala Asn Phe Leu Asn
                 110                 115                 120

Asn Tyr Leu Tyr Asp Gly Glu Glu Ile Ala Thr Arg Gly Asn Val Ile
                 125                 130                 135

Val Val Thr Phe Asn Tyr Arg Val Gly Pro Leu Gly Phe Leu Ser Thr
                 140                 145                 150

Gly Asp Ala Asn Leu Pro Gly Asn Tyr Gly Leu Arg Asp Gln His Met
 155                 160                 165

Ala Ile Ala Trp Val Lys Arg Asn Ile Ala Ala Phe Gly Gly Asp Pro
 170                 175                 180                 185

Asn Asn Ile Thr Leu Phe Gly Glu Ser Ala Gly Gly Ala Ser Val Ser
                 190                 195                 200

Leu Gln Thr Leu Ser Pro Tyr Asn Lys Gly Leu Ile Arg Arg Ala Ile
                 205                 210                 215

Ser Gln Ser Gly Val Ala Leu Ser Pro Trp Val Ile Gln Lys Asn Pro
     220                 225                 230

Leu Phe Trp Ala Lys Lys Val Ala Glu Lys Val Gly Cys Pro Val Gly
         235                 240                 245

Asp Ala Ala Arg Met Ala Gln Cys Leu Lys Val Thr Asp Pro Arg Ala
 250                 255                 260                 265

Leu Thr Leu Ala Tyr Lys Val Pro Leu Ala Gly Leu Glu Tyr Pro Met
                 270                 275                 280

Leu His Tyr Val Gly Phe Val Pro Val Ile Asp Gly Asp Phe Ile Pro
                 285                 290                 295

Ala Asp Pro Ile Asn Leu Tyr Ala Asn Ala Ala Asp Ile Asp Tyr Ile
                 300                 305                 310

Ala Gly Thr Asn Asn Met Asp Gly His Ile Phe Ala Ser Ile Asp Met
                 315                 320                 325

Pro Ala Ile Asn Lys Gly Asn Lys Lys Val Thr Glu Glu Asp Phe Tyr
 330                 335                 340                 345

Lys Leu Val Ser Glu Phe Thr Ile Thr Lys Gly Leu Arg Gly Ala Lys
                 350                 355                 360
```

```
Thr Thr Phe Asp Val Tyr Thr Glu Ser Trp Ala Gln Asp Pro Ser Gln
                365                 370                 375
Glu Asn Lys Lys Thr Val Val Asp Phe Glu Thr Asp Val Leu Phe
        380                 385                 390
Leu Val Pro Thr Glu Ile Ala Leu Ala Gln His Arg Ala Asn Ala Lys
    395                 400                 405
Ser Ala Lys Thr Tyr Ala Tyr Leu Phe Ser His Pro Ser Arg Met Pro
410                 415                 420                 425
Val Tyr Pro Lys Trp Val Gly Ala Asp His Ala Asp Asp Ile Gln Tyr
                430                 435                 440
Val Phe Gly Lys Pro Phe Ala Thr Pro Thr Gly Tyr Arg Pro Gln Asp
            445                 450                 455
Arg Thr Val Ser Lys Ala Met Ile Ala Tyr Trp Thr Asn Phe Ala Lys
            460                 465                 470
Thr Gly Asp Pro Asn Met Gly Asp Ser Ala Val Pro Thr His Trp Glu
        475                 480                 485
Pro Tyr Thr Thr Glu Asn Ser Gly Tyr Leu Glu Ile Thr Lys Lys Met
490                 495                 500                 505
Gly Ser Ser Ser Met Lys Arg Ser Leu Arg Thr Asn Phe Leu Arg Tyr
                510                 515                 520
Trp Thr Leu Thr Tyr Leu Ala Leu Pro Thr Val Thr Asp Gln Glu Ala
            525                 530                 535
Thr Pro Val Pro Pro Thr Gly Asp Ser Glu Ala Thr Pro Val Pro Pro
            540                 545                 550
Thr Gly Asp Ser Glu Thr Ala Pro Val Pro Pro Thr Gly Asp Ser Gly
        555                 560                 565
Ala Pro Pro Val Pro Pro Thr Gly Asp Ser Gly Ala Pro Pro Val Pro
570                 575                 580                 585
Pro Thr Gly Asp Ser Gly Ala Pro Pro Val Pro Pro Thr Gly Asp Ser
                590                 595                 600
Gly Ala Pro Pro Val Pro Pro Thr Gly Asp Ser Gly Ala Pro Pro Val
            605                 610                 615
Pro Pro Thr Gly Asp Ser Gly Ala Pro Pro Val Pro Pro Thr Gly Asp
            620                 625                 630
Ser Gly Ala Pro Pro Val Pro Pro Thr Gly Asp Ala Gly Pro Pro Pro
    635                 640                 645
Val Pro Pro Thr Gly Asp Ser Gly Ala Pro Pro Val Pro Pro Thr Gly
650                 655                 660                 665
Asp Ser Gly Ala Pro Pro Val Thr Pro Thr Gly Asp Ser Glu Thr Ala
                670                 675                 680
Pro Val Pro Pro Thr Gly Asp Ser Gly Ala Pro Pro Val Pro Pro Thr
            685                 690                 695
Gly Asp Ser Glu Ala Ala Pro Val Pro Pro Thr Asp Asp Ser Lys Glu
        700                 705                 710
Ala Gln Met Pro Ala Val Ile Arg Phe
    715                 720

<210> SEQ ID NO 3
<211> LENGTH: 20
<212> TYPE: DNA
<213> ORGANISM: Artificial
<220> FEATURE:
<223> OTHER INFORMATION: Primer
```

```
<400> SEQUENCE: 3
tcccgggacc tgcccgttat                                               20

<210> SEQ ID NO 4
<211> LENGTH: 20
<212> TYPE: DNA
<213> ORGANISM: Artificial
<220> FEATURE:
<223> OTHER INFORMATION: Primer

<400> SEQUENCE: 4
ctgcagagag acgctggcac                                               20
```